(12) United States Patent
Guillaumet et al.

(10) Patent No.: US 6,313,160 B1
(45) Date of Patent: Nov. 6, 2001

(54) SUBSTITUTED HETEROCYCLIC COMPOUNDS, METHOD FOR PREPARING AND COMPOSITIONS CONTAINING SAME

(75) Inventors: Gérald Guillaumet, Saint Jean Le Blanc; Marie-Claude Viaud; Ahmed Mamai, both of Orleans; Isabelle Charton, Yerres; Pierre Renard, Le Chesnay; Caroline Bennejean, Charenton Le Pont; Béatrice Guardiola, Saint Cloud; Philippe Daubos, Mardie, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/423,745

(22) PCT Filed: May 14, 1998

(86) PCT No.: PCT/FR98/00954

§ 371 Date: Nov. 12, 1999

§ 102(e) Date: Nov. 12, 1999

(87) PCT Pub. No.: WO98/52935

PCT Pub. Date: Nov. 26, 1998

(30) Foreign Application Priority Data

May 16, 1997 (FR) .................................................. 97 06019

(51) Int. Cl.⁷ .......................... C07D 311/58; A61K 31/35
(52) U.S. Cl. .......................... 514/430; 514/456; 549/23; 549/406; 549/407

(58) Field of Search .............................. 549/23, 406, 407; 514/430, 456

(56) References Cited

U.S. PATENT DOCUMENTS 5,308,866 * 5/1994 Lesieur et al. ....................... 549/467

* cited by examiner

*Primary Examiner*—Bernard Dentz
(74) *Attorney, Agent, or Firm*—The Firm of Hueschen and Sage; G. Patrick Sage

(57) ABSTRACT

The invention relates to compounds of formula (I):

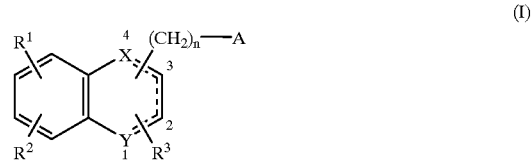

wherein:
$R^1$, $R^2$ and $R^3$ are as defined in the description,
X is as defined in the description,
Y represents an oxygen atom, a sulphur atom, a $C(H)_q$ group, SO or $SO_2$,
n is equal to from 0 to 5,
A represents a $NR^5R^6$ group,
and medicinal products containing the same which are useful in treating or in preventing melatoninergic disorders.

11 Claims, No Drawings

SUBSTITUTED HETEROCYCLIC COMPOUNDS, METHOD FOR PREPARING AND COMPOSITIONS CONTAINING SAME

The present application is a U.S. National Application filed under 35 USC 371 of PCT/FR98/00954, filed May 14, 1998, based upon French application Serial No. 97.06019 filed May 16, 1997.

FIELD OF THE INVENTION

The present invention relates to new substituted heterocyclic compounds.

DESCRIPTION OF THE PRIOR ART

The new compounds have proved to be very powerfull ligands for melatoninergic receptors.

From the prior art there are known benzoxazin compounds used as fungicides (Hahn H. G. et al., J. Korean Chem. Soc., 1994, 38(10), pp. 776–81) or as lipogenesis inhibitors in mammals (U.S. Pat. No. 4,308,276).

Also known are a large number of (dihydro)chromene compounds as 5HT ligands for use in the treatment of hypertension, depression or anxiety (WO 9426703, DE 4135474), or dopaminergic receptor agonists (WO 9608489) for use in the treatment of cardiovascular diseases.

(Dihydro)benzodioxin compounds are furthermore described as anti-oxidants and inhibitors of lipid peroxidation (EP 624582), or for use in the treatment of liver diseases (J07242655 and J07242543), or as α-adrenergic receptor blockers (Dewar G. H. et al., Eur. J. Med. Chem.—Chim. Ther., 1983, 18(3), pp 286–90).

BACKGROUND OF THE INVENTION

In the last ten years, numerous studies have demonstrated the major role played by melatonin (5-methoxy-N-acetyltryptamine) in the control of the circadian rhythm and of endocrinal functions. In addition, melatonin receptors have been characterised and located.

In addition to their beneficial action on circadian rhythm disorders (J. Neurosurg. 1985, 63, pp 321–341) and sleep disorders (Psychopharmacology, 1990, 100, pp 222–226), ligands for the melatoninergic system have valuable pharmacological properties in respect of the central nervous system, especially anxiolytic and antipsychotic properties (Neuropharmacology of Pineal Secretions, 1990, 8 (3–4), pp 264–272) and analgesic properties (Pharmacopsychiat., 1987, 20, pp 222–223) and also for the treatment of Parkinson's disease (J. Neurosurg. 1985, 63, pp 321–341) and Alzheimer's disease (Brain Research, 1990, 528, pp 170–174). Those compounds have also exhibited activity in respect of certain cancers (Melatonin—Clinical Perspectives, Oxford University Press, 1988, pp 164–165), ovulation (Science 1987, 227, pp 714–720) and diabetes (Clinical Endocrinology, 1986, 24, pp 359–364), and in the treatment of obesity (International Journal of Eating Disorders, 1996, 20 (4), pp 443–446).

Compounds providing a means of acting on the melatoninergic system are accordingly excellent medicaments for the clinician for the treatment of pathologies associated with the melatoninergic system, especially those mentioned above.

DETAILED DESCRIPTION OF THE INVENTION

The present invention relates more especially to compounds of formula (I):

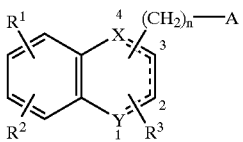

wherein

R$^1$ represents a hydrogen atom, a substituted or unsubstituted linear or branched ($C_1$–$C_6$)alkyl group, a substituted or unsubstituted linear or branched ($C_2$–$C_6$) alkenyl group, a substituted or unsubstituted linear or branched ($C_2$–$C_6$)alkynyl group, a substituted or unsubstituted ($C_3$–$C_8$)cycloalkyl group, a substituted or unsubstituted ($C_3$–$C_8$)cycloalkyl-($C_1$–$C_6$)alkyl group in which the alkyl moiety is linear or branched, or an OR$^4$ group (wherein R$^4$ represents a hydrogen atom, a substituted or unsubstituted linear or branched ($C_1$–$C_6$) alkyl group, a substituted or unsubstituted linear or branched ($C_2$–$C_6$)alkenyl group, a substituted or unsubstituted linear or branched ($C_2$–$C_6$)alkynyl group, an aryl group, an aryl-($C_1$–$C_6$)alkyl group in which the alkyl moiety is linear or branched, a substituted or unsubstituted ($C_3$–$C_8$)cycloalkyl group or a substituted or unsubstituted ($C_3$–$C_8$)cycloalkyl-($C_1$–$C_6$)alkyl group in which the alkyl moiety is linear or branched, R$^2$ represents a hydrogen atom, or R$^1$ and R$^2$, located on two adjacent carbon atoms, form together with the carbon atoms that carry them an aryl group, or a 6-membered ring containing one or two oxygen atoms, X represents an oxygen atom, a sulphur atom, a C(H)$_q$ group (wherein q is equal to 0, 1 or 2), SO, SO$_2$, or X represents a single bond when R$^1$ and R$^2$, located on two adjacent carbon atoms, form together with the carbon atoms that carry them an aryl group, or a 6-membered ring containing two oxygen atoms, Y represents an oxygen atom, a sulphur atom, a C(H)$_q$ group (wherein q is equal to 0, 1 or 2), SO or SO$_2$, it being understood that X and Y cannot simultaneously represent a C(H)$_q$ group (wherein q is equal to 0, 1 or 2), R$^3$ represents a hydrogen atom, an aryl group, an aryl-($C_1$–$C_6$)alkyl group in which the alkyl moiety is linear or branched, or a linear or branched ($C_1$–$C_6$)alkyl group, n is equal to 0, 1, 2, 3, 4 or 5 when R$^1$ and R$^2$, located on two adjacent carbon atoms, form together with the carbon atoms that carry them an aryl group, or a 6-membered ring containing one or two oxygen atoms, or n is equal to 1, 2, 3, 4 or 5 when R$^1$ is as defined hereinabove and R$^2$ represents a hydrogen atom, it being possible for the —(CH$_2$)$_n$— chain to be substituted by one or more halogen atoms or one or more identical or different groups selected from linear or branched ($C_1$–$C_6$)alkyl, OH, linear or branched ($C_1$–$C_6$)alkylcarbonyl and linear or branched ($C_1$–$C_6$)alkoxycarbonyl, A represents a NR$^5$R$^6$ group wherein R$^6$ represents a hydrogen atom or a linear or branched ($C_1$–$C_6$)alkyl group, $R^5$ represents a

group wherein Z represents an oxygen atom or a sulphur atom, and $R^7$ represents:
  a hydrogen atom,
    an $R^8$ group which represents a substituted or unsubstituted linear or branched $(C_1-C_6)$alkyl group, a substituted or unsubstituted $(C_3-C_8)$ cycloalkyl group, a substituted or unsubstituted $(C_3-C_8)$cycloalkyl-$(C_1-C_6)$alkyl group in which the alkyl moiety is linear or branched, a substituted or unsubstituted linear or branched $(C_2-C_6)$alkenyl group, a substituted or unsubstituted linear or branched $(C_2-C_6)$ alkynyl group, an aryl group or an aryl-$(C_1-C_6)$alkyl group in which the alkyl moiety is linear or branched,
    or a $NR^8R^9$ group wherein $R^9$ represents a hydrogen atom or a linear or branched $(C_1-C_6)$alkyl group and $R^8$ is as defined hereinabove,
  or a

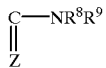

group wherein Z, $R^8$ and $R^9$ are as defined hereinabove,
the symbol

means that the bonds can be single or double, it being understood that two adjacent bonds cannot simultaneously be double and that the valency of the atoms is respected,
  it being understood that:
    the term "aryl" denotes a phenyl or naphthyl group optionally substituted by one or more halogen atoms or one or more identical or different groups selected from OH, linear or branched $(C_1-C_6)$alkoxy, linear or branched $(C_1-C_6)$alkyl, cyano, nitro, amino, alkylamino, dialkylamino and trihaloalkyl,
    the term "substituted" used in respect of the terms "alkyl", "alkenyl" and "alkynyl" means that the group is substituted by one or more halogen atoms or one or more identical or different groups selected from OH, linear or branched $(C_1-C_6)$alkoxy, amino, alkylamino and dialkylamino,
    the term "substituted" used in respect of the terms "cycloalkyl" and "cycloalkylalkyl" means that the cyclic moiety is substituted by one or more halogen atoms or one or more identical or different groups selected from linear or branched $(C_1-C_6)$alkyl, linear or branched $(C_1-C_6)$alkoxy, hydroxy, oxo, amino, alkylamino and dialkylamino,
  provided that:
    when the compound of formula (I) is a 2,3-dihydro-1,4-benzodioxin compound (X and Y simultaneously represent an oxygen atom, $R^1$, $R^2$ and $R^3$ simultaneously represent a hydrogen atom and the bonds ==== are single), the group —$(CH_2)_n$—A is other than the following groups:
      —$CH_2$—$NHCOR_a$ (wherein $R_a$ represents an ethyl, 3,4,5-trimethoxyphenyl, 2,6-dimethoxyphenylethyl, phenylethyl, benzyl, phenyl, chloromethyl or trifluoromethyl group),
      —$(CH_2)_2$—$NHCOR_b$ (wherein $R_b$ represents a 2,3,4-trimethoxyphenyl group),
      —$CH_2$—$CONHR_c$ (wherein $R_c$ represents a methyl, ethyl, n-butyl, 2-hydroxypropyl or 3-methoxypropyl group),
      —$(CH_2)_2$—$CONHR_d$ (wherein $R_d$ represents a methyl, 2-hydroxypropyl or 3-hydroxypropyl group),
    when the compound of formula (I) is a chroman compound (X represents a $CH_2$ group, Y represents an oxygen atom and $R^1$, $R^2$ and $R^3$ are as defined hereinabove and the bonds ==== are single), the group —$(CH_2)_n$—A is other than the following groups:
      —$CH_2$—$NHCOR_e$ (wherein $R_e$ represents a cycloalkyl group) in the 2-position of the chroman group,
      —$CH_2$—$CONHR_f$ (wherein $R_f$ represents a benzyl or 1-phenyl-2-hydroxyethyl group) in the 4-position of the chroman group,
    when A represents a $NHCSNHR^8$ group and n is equal to 2, $R^8$ cannot represent an aryl group,
    when X represents a $CH_2$ group, $R^1$ is as defined hereinabove and $R^2$ represents a hydrogen atom, A cannot represent a urea or thiourea group substituted by a substituted or unsubstituted phenyl group,
    the compound of formula (I) cannot represent a thiochroman group (X represents a $CH_2$ group, Y represents a sulphur atom, $R^1$ is as defined hereinabove and $R^2$ represents a hydrogen atom) substituted in the 3-position by a

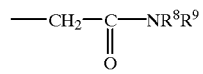

chain wherein $R^8$ and $R^9$ are as defined hereinabove,
  their enantiomers and diastereoisomers, and addition salts thereof with a pharmaceutically acceptable acid or base.

Among the pharmaceutically acceptable acids there may mentioned by way of non-limiting examples hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, etc.

Among the pharmaceutically acceptable bases there may be mentioned by way of non-limiting examples sodium hydroxide, potassium hydroxide, triethylamine, tert-butylamine, etc.

An advantageous variant of the present invention relates to compounds of formula (I):

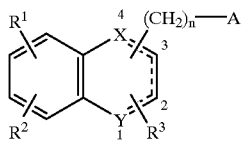
(I)

wherein:

R¹ represents a hydrogen atom, a substituted or unsubstituted linear or branched ($C_1$–$C_6$)alkyl group, a substituted or unsubstituted linear or branched ($C_2$–$C_6$) alkenyl group, a substituted or unsubstituted linear or branched ($C_2$–$C_6$)alkynyl group, a substituted or unsubstituted ($C_3$–$C_8$)cycloalkyl group, a substituted or unsubstituted ($C_3$–$C_8$)cycloalkyl-($C_1$–$C_6$)alkyl group in which the alkyl moiety is linear or branched, or an OR⁴ group (wherein R⁴ represents a hydrogen atom, a substituted or unsubstituted linear or branched ($C_1$–$C_6$) alkyl group, a substituted or unsubstituted linear or branched ($C_2$–$C_6$)alkenyl group, a substituted or unsubstituted linear or branched ($C_2$–$C_6$)alkynyl group, an aryl group, an aryl-($C_1$–$C_6$)alkyl group in which the alkyl moiety is linear or branched, a substituted or unsubstituted ($C_3$–$C_8$)-cycloalkyl group or a substituted or unsubstituted ($C_3$–$C_8$)cycloalkyl-($C_1$–$C_6$)alkyl group in which the alkyl moiety is linear or branched), R² represents a hydrogen atom, or R¹ and R², located on two adjacent carbon atoms, form together with the carbon atoms that carry them an aryl group, or a 6-membered ring containing one or two oxygen atoms, X represents an oxygen atom, a sulphur atom, a C(H)$_q$ group (wherein q is equal to 0, 1 or 2), SO or SO₂, Y represents an oxygen atom, a sulphur atom, a C(H)$_q$ group (wherein q is equal to 0, 1 or 2), SO or SO₂,
it being understood that X and Y cannot simultaneously represent a C(H)$_q$ group (wherein q is equal to 0, 1 or 2), R³ represents a hydrogen atom, an aryl group, an aryl-($C_1$–$C_6$)alkyl group in which the alkyl moiety is linear or branched, or a linear or branched ($C_1$–$C_6$)alkyl group, n is equal to 0, 1, 2, 3, 4 or 5 when R¹ and R², located on two adjacent carbon atoms, form together with the carbon atoms that carry them an aryl group, or a 6-membered ring containing one or two oxygen atoms, or n is equal to 1, 2, 3, 4 or 5 when R¹ is as defined hereinabove and R² represents a hydrogen atom,
it being possible for the —(CH₂)$_n$— chain to be substituted by one or more halogen atoms or one or more identical or different groups selected from linear or branched ($C_1$–$C_6$)alkyl, OH, linear or branched ($C_1$–$C_6$)alkoxy, linear or branched ($C_1$–$C_6$) alkylcarbonyl and linear or branched ($C_1$–$C_6$) alkoxycarbonyl, A represents
a NR⁵R⁶ group wherein
R⁶ represents a hydrogen atom or a linear or branched ($C_1$–$C_6$)alkyl group R⁵ represents a

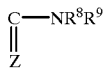

group wherein Z represents an
oxygen atom or a sulphur atom, and R⁷ represents:
a hydrogen atom,
an R⁸ group which represents a substituted or unsubstituted linear or branched ($C_1$–$C_6$)alkyl group, a substituted or unsubstituted ($C_3$–$C_8$) cycloalkyl group, a substituted or unsubstituted ($C_3$–$C_8$)cycloalkyl-($C_1$–$C_6$)alkyl group in which the alkyl moiety is linear or branched, a substituted or unsubstituted linear or branched ($C_2$–$C_6$)alkenyl group, a substituted or unsubstituted linear or branched ($C_2$–$C_6$) alkynyl group, an aryl group or an aryl-($C_1$–$C_6$)alkyl group in which the alkyl moiety is linear or branched,
or a NR⁸R⁹ group wherein R⁹ represents a hydrogen atom or a linear or branched ($C_1$–$C_6$)alkyl group and R⁸ is as defined hereinabove, or a

group wherein Z, R⁸ and R⁹ are as defined hereinabove,
the symbol

means that the bonds can be single or double, it being understood that two adjacent bonds cannot simultaneously be double and that the valency of the atoms is respected,
it being understood that:
the term "aryl" denotes a phenyl or naphthyl group optionally substituted by one or more halogen atoms or one or more identical or different groups selected from OH, linear or branched ($C_1$–$C_6$)alkoxy, linear or branched ($C_1$–$C_6$)alkyl, cyano, nitro, amino, alkylamino, dialkylamino and trihaloalkyl,
the term "substituted" used in respect of the terms "alkyl", "alkenyl" and "alkynyl" means that the group is substituted by one or more halogen atoms or one or more identical or different groups selected from OH, linear or branched ($C_1$–$C_6$)alkoxy, amino, alkylamino and dialkylamino,
the term "substituted" used in respect of the terms "cycloalkyl" and "cycloalkylalkyl" means that the cyclic moiety is substituted by one or more halogen atoms or one or more identical or different groups selected from linear or branched ($C_1$–$C_6$)alkyl, linear or branched ($C_1$–$C_6$)alkoxy, hydroxy, oxo, amino, alkylamino and dialkylamino,
provided that:
when the compound of formula (I) is a 2,3-dihydro-1,4-benzodioxin compound (X and Y simultaneously represent an oxygen atom, R¹, R² and R³ simultaneously represent a hydrogen atom and the bonds ═══ are single), the group —(CH$_2$)$_n$—A is other than the following groups:
- —CH$_2$—NHCOR$_a$ (wherein R$_a$ represents an ethyl, 3,4,5-trimethoxyphenyl, 2,6-dimethoxyphenylethyl, phenylethyl, benzyl, phenyl, chloromethyl or trifluoromethyl group),
- —(CH$_2$)$_2$—NHCOR$_b$ (wherein R$_b$ represents a 2,3,4-trimethoxyphenyl group),
- —CH$_2$—CONHR$_c$ (wherein R$_c$ represents a methyl, ethyl, n-butyl, 2-hydroxypropyl or 3-methoxypropyl group),
- —(CH$_2$)$_2$—CONHR$_d$ (wherein R$_d$ represents a methyl, 2-hydroxypropyl or 3-hydroxypropyl group), when the compound of formula (I) is a chroman compound (X represents a CH$_2$ group, Y represents an oxygen atom and R$^1$, R$^2$ and R$^3$ are as defined hereinabove and the bonds ═══ are single), the group —(CH$_2$)$_n$—A is other than the following groups:
- —CH$_2$—NHCOR$_e$ (wherein R$_e$ represents a cycloalkyl group) in the 2-position of the chroman group,
- —CH$_2$—CONHR$_f$ (wherein R$_f$ represents a benzyl or 1-phenyl-2-hydroxyethyl group) in the 4-position of the chroman group, when A represents a NHCSNHR$^8$ group and n is equal to 2, R$^8$ cannot represent an aryl group, when X represents a CH$_2$ group, R$^1$ is as defined hereinabove and R$^2$ represents a hydrogen atom, A cannot represent a urea or thiourea group substituted by a substituted or unsubstituted phenyl group, the compound of formula (I) cannot represent a thiochroman group (X represents a CH$_2$ group, Y represents a sulphur atom, R$^1$ is as defined hereinabove and R$^2$ represents a hydrogen atom) substituted in the 3-position by a

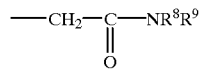

chain wherein R$^8$ and R$^9$ are as defined hereinabove, their enantiomers and diastereoisomers, and addition salts thereof with a pharmaceutically acceptable acid or base.

Another advantageous variant of the present invention relates to compounds of formula (I):

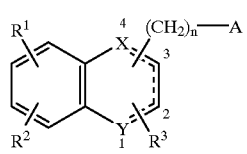

(I)

wherein:
R$^1$ and R$^2$, located on two adjacent carbon atoms, form together with the carbon atoms that carry them an aryl group, or a 6-membered ring containing two oxygen atoms,
X represents a single bond,
Y represents an oxygen atom, a sulphur atom, a C(H)$_q$ group (wherein q is equal to 0, 1 or 2), SO or SO$_2$,
R$^3$ represents a hydrogen atom, an aryl group, an aryl-(C$_1$-C$_6$)alkyl group in which the alkyl moiety is linear or branched, or a linear or branched (C$_1$-C$_6$)alkyl group,
n is equal to 0, 1, 2, 3, 4 or 5, it being possible for the —(CH$_2$)$_n$— chain to be substituted by one or more halogen atoms or one or more identical or different groups selected from linear or branched (C$_1$-C$_6$)alkyl, OH, linear or branched (C$_1$-C$_6$)alkoxy, linear or branched (C$_1$-C$_6$)alkylcarbonyl and linear or branched (C$_1$-C$_6$)alkoxycarbonyl,
A represents
a NR$^5$R$^6$ group wherein
R$^6$ represents a hydrogen atom or a linear or branched (C$_1$-C$_6$)alkyl group,
R$^5$ represents a

group wherein Z represents an oxygen atom or a sulphur atom, and R$^7$ represents:
a hydrogen atom,
an R$^8$ group which represents a substituted or unsubstituted linear or branched (C$_1$-C$_6$)alkyl group, a substituted or unsubstituted (C$_3$-C$_8$) cycloalkyl group, a substituted or unsubstituted (C$_3$-C$_8$)cycloalkyl-(C$_1$-C$_6$)alkyl group in which the alkyl moiety is linear or branched, a substituted or unsubstituted linear or branched (C$_2$-C$_6$)alkenyl group, a substituted or unsubstituted linear or branched (C$_2$-C$_6$) alkynyl group, an aryl group or an aryl-(C$_1$-C$_6$)alkyl group in which the alkyl moiety is linear or branched,
or a NR$^8$R$^9$ group wherein R$^9$ represents a hydrogen atom or a linear or branched (C$_1$-C$_6$)alkyl group and R$^8$ is as defined hereinabove,
or a

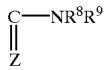

group wherein Z, R$^8$ and R$^9$ are as defined hereinabove,
the symbol

means that the bonds can be single or double, it being understood that two adjacent bonds cannot simultaneously be double and that the valency of the atoms is respected,
it being understood that:
the term "aryl" denotes a phenyl or naphthyl group optionally substituted by one or more halogen atoms or one or more identical or different groups selected from OH, linear or branched (C$_1$-C$_6$)alkoxy, linear or branched (C$_1$-C$_6$)alkyl, cyano, nitro, amino, alkylamino, dialkylamino and trihaloalkyl, the term "substituted" used in respect of the terms "alkyl", "alkenyl" and "alkynyl" means that the group is substituted by one or more halogen atoms or one or more identical or different groups selected from OH, linear or branched ($C_1$–$C_6$)alkoxy, amino, alkylamino and dialkylamino, the term "substituted" used in respect of the terms "cycloalkyl" and "cycloalkylalkyl" means that the cyclic moiety is substituted by one or more halogen atoms or one or more identical or different groups selected from linear or branched ($C_1$–$C_6$)alkyl, linear or branched ($C_1$–$C_6$)-alkoxy, hydroxy, oxo, amino, alkylamino and dialkylamino, provided that:
when A represents a NHCSNHR$^8$ group and n is equal to 2, R$^8$ cannot represent an aryl group,
their enantiomers and diastereoisomers, and addition salts thereof with a pharmaceutically acceptable acid or base.

The preferred compounds of the invention are the compounds of formula (I) wherein:
R$^1$ and R$^2$, located on two adjacent carbon atoms, form together with the carbon atoms that carry them a phenyl or substituted phenyl group,
R$^1$ and R$^2$, located on two adjacent carbon atoms, form together with the carbon atoms that carry them a 6-membered ring containing one or two oxygen atoms,
R$^1$ represents an OR$^4$ group,
X represents a C(H)$_q$ group (wherein q is equal to 0, 1 or 2) and Y represents an oxygen or sulphur atom,
X and Y simultaneously represent an oxygen or sulphur atom,
X represents a single bond,
R$^3$ represents a hydrogen atom,
R$^3$ represents an aryl group,
A represents a group of formula NR$^5$R$^6$.

More especially, the present invention relates to dihydrobenzochromene, dihydrochromene, chromene and dihydro-6,7-ethylenedioxy-chromene compounds.

More especially still, the present invention relates to the compounds of formula (I) which are:
N-(9-methoxy-2,3-dihydro-1H-benzo[f]chromen-2-yl)acetamide
N-[2-(6-methoxy-3,4-dihydro-2H-chromenyl)ethyl]acetamide
N-[(6-methoxy-2H-3-chromenyl)methyl]butanamide.

The isomers and the addition salts, with a pharmaceutically acceptable acid or base, of the preferred compounds of the invention form an integral part of the invention.

The invention relates also to a process for the preparation of compounds of formula (I), characterised in that there is used as starting material a compound of formula (II):

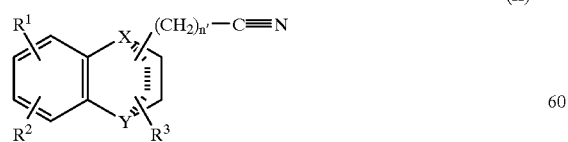
(II)

wherein R$^1$, R$^2$, R$^3$, X and Y are as defined hereinabove, and n' can have the values from 0 to 4,
which is subjected:
to a reducing agent to yield a compound of formula (III):

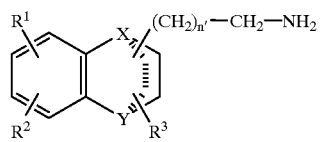
(III)

wherein R$^1$, R$^2$, R$^3$, X, Y and n' are as defined hereinabove, which compounds of formula (III) can, moreover, be obtained
by reduction of a compound of formula (IV):

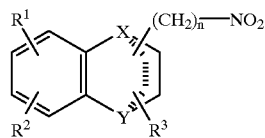
(IV)

wherein R$^1$, R$^2$, R$^3$, X, Y and n are as defined hereinabove,
or starting from a compound of formula (V):

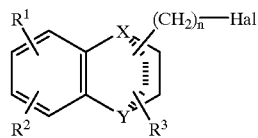
(V)

wherein R$^1$, R$^2$, R$^1$, X, Y and n are as defined hereinabove and Hal represents a halogen atom,
which is substituted by a phthalimide group and is then subjected to hydrazinolysis,
with which compound of formula (III) there is condensed:
either an acyl chloride ClCOR$^8$ or the corresponding acid anhydride (mixed or symmetrical) wherein R$^8$ is as defined hereinabove,
to yield a compound of formula (I/a), which is a particular case of the compounds of formula (I):

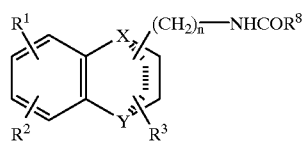
(I/a)

wherein R$^1$, R$^2$, R$^3$, R$^8$, X, Y and n are as defined hereinabove,
which can be subjected to a thionisation agent, such as Lawesson's reagent, to obtain a compound of formula (I/b), which is a particular case of the compounds of formula (I):

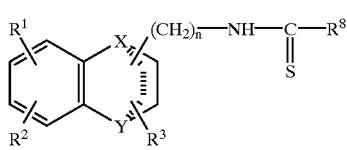
(I/b)

wherein $R^1$, $R^2$, $R^3$, $R^8$, X, Y and n are as defined hereinabove,
or a compound of formula (VI):

$$Z=C=N-R^8 \quad (VI)$$

wherein Z and $R^8$ are as defined hereinabove,
in order to obtain a compound of formula (I/c), which is a particular case of the compounds of formula (I):

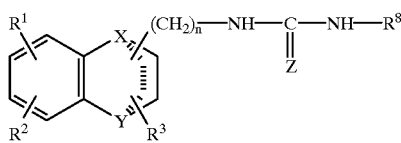
(I/c)

wherein $R^1$, $R^2$, $R^3$, $R^8$, X, Y, Z and n are as defined hereinabove,
the totality of the compounds of formulae (I/a), (I/b) and (I/c) constituting the compound of formula (I/d), which is a particular case of the compounds of formula (I):

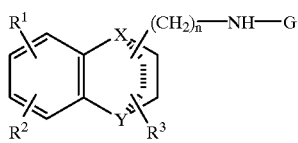
(I/d)

wherein $R^1$, $R^2$, $R^3$, X, Y and n are as defined hereinabove, and G represents a $COR^8$, $CSR^8$ or $CZNHR^8$ group wherein Z and $R^8$ are as defined hereinabove,
which can be alkylated in accordance with a conventional alkylation technique using a compound of formula (VII):

$$\text{Alk-W} \quad (VII)$$

wherein Alk represents a linear or branched ($C_1$–$C_6$) alkyl group and W represents a leaving group, such as a halogen atom or a tosyl group,
or using a dialkyl sulphate,
to yield a compound of formula (I/e), which is a particular case of the compounds of formula (I):

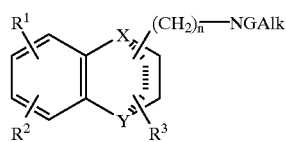
(I/e)

wherein $R^1$, $R^2$, $R^3$, X, Y, G, Alk and n are as defined hereinabove,
or to hydrolysis in an acidic or basic medium to yield a compound of formula (VIII):

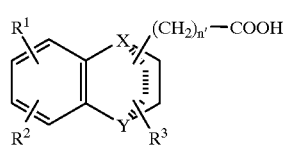
(VIII)

wherein $R^1$, $R^2$, $R^3$, X, Y and n' are as defined hereinabove,
which is subjected, after activation to the acid chloride form or in the presence of a coupling agent, to the action of an amine $H_2NR^8$ wherein $R^8$ is as defined hereinabove,
to yield a compound of formula (I/f), which is a particular case of the compounds of formula (I):

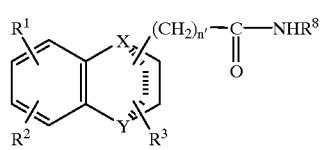
(I/f)

wherein $R^1$, $R^2$, $R^3$, $R^8$, X, Y and n' are as defined hereinabove,
which can be subjected to a thionisation agent, such as Lawesson's reagent, to obtain a compound (I/g), which is a particular case of the compounds of formula (I):

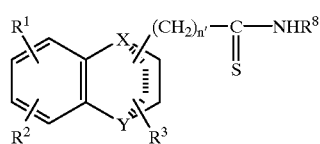
(I/g)

wherein $R^1$, $R^2$, $R^3$, $R^8$, X, Y and n' are as defined hereinabove,
the totality of the compounds (I/f) and (I/g) constituting the compound of formula (I/h):

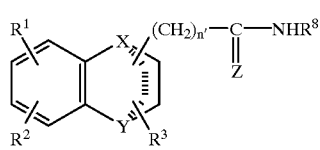

(I/h)

wherein $R^1$, $R^2$, $R^3$, $R^8$, X, Y, Z and n' are as defined hereinabove, which can be alkylated in accordance with a conventional alkylation technique to yield a compound of formula (I/i):

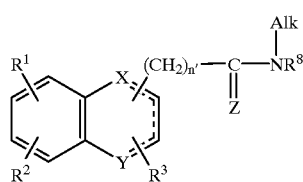

(I/i)

wherein $R^1$, $R^2$, $R^3$, $R^8$, X, Y, Z, Alk and n' are as defined hereinabove, the compounds of formulae (I/a) to (I/i) constituting the totality of the compounds of formula (I), which can be purified in accordance with a conventional separation technique, are converted, if desired, into their addition salts with a pharmaceutically acceptable acid or base and, optionally, are separated into their isomers in accordance with a conventional separation technique.

The compounds of formula (II) are obtained inter alia:

starting from compounds of formula (IX):

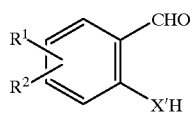

(IX)

wherein $R^1$ and $R^2$ are as defined hereinabove and X' represents a sulphur atom or an oxygen atom, which is condensed with acrylonitrile, to yield a compound of formula (II/a), which is a particular case of the compounds of formula (II):

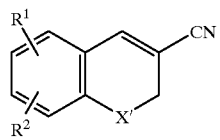

(II/a)

wherein $R^1$, $R^2$ and X' are as defined hereinabove, which is subjected to reduction to obtain a compound of formula (II/b), which is a particular case of the compounds of formula (II):

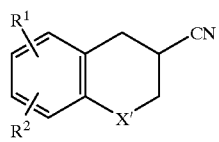

(II/b)

wherein $R^1$, $R^2$ and X' are as defined hereinabove,
starting from compounds of formula (X)):

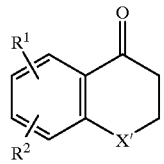

(X)

wherein $R^1$, $R^2$ and X' are as defined hereinabove,
which is subjected to a Wittig reaction followed by catalytic reduction to obtain a compound of formula (II/c), which is a particular case of the compounds of formula (II):

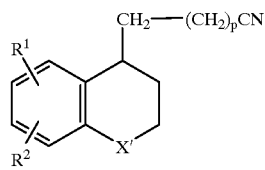

(II/c)

wherein $R^1$, $R^2$ and X' are as defined hereinabove and p is equal to 0, 1, 2, 3 or 4,
starting from compounds of formula (XI):

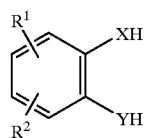

(XI)

wherein $R^1$, $R^2$, X and Y are as defined hereinabove,
with which there is condensed:
chloroacrylonitrile to obtain a compound of formula (II/d), which is a particular case of the compounds of formula (II):

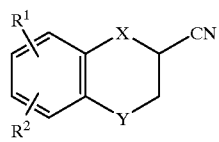

(II/d)

wherein $R^1$, $R^2$, X and Y are as defined hereinabove,
which can be dibrominated and then treated with sodium iodide to yield a compound of formula (II/e), which is a particular case of the compounds of formula (II) :

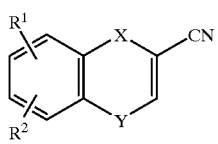
(II/e)

wherein $R^1$, $R^2$, X and Y are as defined hereinabove, or ethyl 2,3-dibromopropionate to yield a compound of formula (XI):

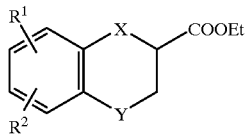
(XII)

wherein $R^1$, $R^2$, X and Y are as defined hereinabove, which can be dibrominated and then treated with sodium iodide to yield a compound of formula (XIII):

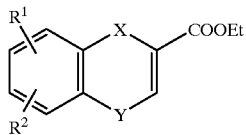
(XIII)

wherein $R^1$, $R^2$, X and Y are as defined hereinabove, the totality of the compounds (XII) and (XIII) constituting the compound of formula (XIV):

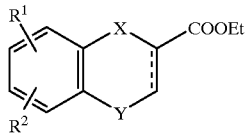
(XIV)

wherein $R^1$, $R^2$, X and Y are as defined hereinabove and the symbol ∥ means that the bond can be single or double, which compound (XIV) is subjected to lithiation followed by condensation with the desired electrophile in order to yield a compound of formula (XV):

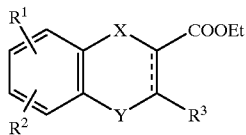
(XV)

wherein $R^1$, $R^2$, $R^3$, X, Y and the symbol ∥ are as defined hereinabove, which may be, in succession, reduced to the corresponding alcohol, oxidised to the aldehyde and subjected to a Wittig reaction to yield a compound of formula (XVI):

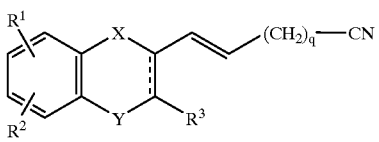
(XVI)

wherein $R^1$, $R^2$, $R^3$, X, Y and the symbol ∥ are as defined hereinabove and q is equal to 0, 1, 2 or 3, which is reduced catalytically to yield a compound of formula (II/f), which is a particular case of the compounds of formula (II):

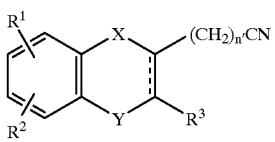
(II/f)

wherein $R^1$, $R^2$, $R^3$, X, Y, n' and the symbol ∥ are as defined hereinabove.

The invention relates also to a process for the preparation of compounds of formula (I) wherein X represents a single bond, characterised in that a compound of formula (XVII):

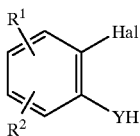
(XVII)

wherein Y, $R^1$ and $R^2$ are as defined hereinabove and Hal represents a halogen atom, is condensed with a compound of formula (XVIII):

$$R^3\!-\!C\!\equiv\!C\!-\!(CH_2)_n\!-\!A \quad (XVIII)$$

wherein $R^3$, n and A are as defined hereinabove, to obtain a compound of formula (I/j), which is a particular case of the compounds of formula (I):

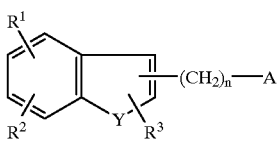
(I/j)

wherein $R^1$, $R^2$, $R^3$, Y, n and A are as defined hereinabove, which compounds of formula (I/j) can be purified in accordance with a conventional separation technique, are converted, if desired, into their addition salts with a pharmaceutically acceptable acid or base and, optionally, are separated into their isomers in accordance with a conventional separation technique.

The compounds of the invention and the pharmaceutical compositions containing them have proved to be useful in the treatment of disorders of the melatoninergic system.

A pharmacological study of the compounds of the invention has in fact shown them to be non-toxic, to have a very high selective affinity for melatonin receptors and to possess important activities in respect of the central nervous system and, in particular, therapeutic properties in relation to sleep disorders, anxiolytic, antipsychotic and analgesic properties and activity on the microcirculation, enabling it to be established that the products of the invention are useful in the treatment of stress, sleep disorders, anxiety, seasonal affective disorder, cardiovascular pathologies, insomnia and fatigue resulting from jet lag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss, Alzheimer's disease, and also cerebral circulation disorders. In another field of activity, it appears that, in treatment, the products of the invention have ovulation-inhibiting properties and immunomodulating properties and are able to be used in the treatment of cancers. The compounds will preferably be used in the treatment of seasonal affective disorder, sleep disorders, cardiovascular pathologies, insomnia and fatigue resulting from jet lag, appetite disorders and obesity.

For example, the compounds will be used in the treatment of seasonal affective disorder and sleep disorders.

The present invention relates also to pharmaceutical compositions comprising products of formula (I) in combination with one or more pharmaceutically acceptable excipients.

Among the pharmaceutical compositions according to the invention there may be mentioned more especially those that are suitable for oral, parenteral, nasal, percutaneous, transcutaneous, rectal, perlingual, ocular or respiratory administration and especially tablets, dragees, sublingual tablets, sachets, paquets, gelatin capsules, glossettes, lozenges, suppositories, creams, ointments, dermal gels and drinkable or injectable ampoules.

The dosage varies according to the sex, age and weight of the patient, the route of administration, the nature of the therapeutic indication, or possible associated treatments, and ranges from 0.01 mg to 1 g per 24 hours in 1 or more administrations.

The following Examples illustrate the invention but do not limit it in any way.

PREPARATION 1

7-Hydroxy-2,3-dihydro-1,4-benzodioxin-6-carbaldehyde

Step A: 2,3-Dihydro-1,4-benzodioxin-6-ol 1 g of 2,3-dihydro-1,4-benzodioxin-6-yl acetate (5.149 mmol) is dissolved in a solution of methanol (7.5 ml) and, under an argon atmosphere, the mixture is made basic, dropwise, with a 10% sodium hydroxide solution. The mixture is stirred at ambient temperature for 4 hours. At the end of the reaction, the methanol is evaporated and the reaction medium is acidified (to pH=1) with a 2N HCl solution and then washed with ethyl acetate. After extraction, drying over $MgSO_4$ is carried out and the product is concentrated in vacuo. Purification on a silica column allows an oil to be obtained (eluant:PE/AcOEt 8/2 then 7/3).

Step B: 6-Methoxy-2,3-dihydro-1,4-benzodioxin 3 g (18.05 mmol) of the alcohol obtained in Step A are dissolved in 10 ml of DMF in a flask. 2 eq. of NaH (60% in oil) are added slowly and allowed to act for 30 minutes under an inert atmosphere. 2 eq. of iodomethane are then added. The mixture is stirred for 2 hours; the DMF is then evaporated. Washing with ethyl acetate and with water is carried out and the two phases are separated. The combined organic phases are dried over $MgSO_4$ and the solvent is evaporated. The oil obtained is purified on a silica column (eluant: PE/AcOEt 8/2), which allows the pure title product to be obtained.

Step C: 7-Methoxy-2,3-dihydro-1,4-benzodioxin-6-carbaldehyde 3.3 eq. of dry DMF are placed in a three-necked flask and then, using a dropping funnel, 1.3 eq. of phosphorus oxychloride are added at 0° C. After returning to ambient temperature, the compound obtained in Step B (4 g:20.59 mmol) is dissolved in 6.5 ml of DMF and then added to the previous solution. Heating is carried out for 2 hours at 110° C. After cooling, the mixture is hydrolysed with water and extracted with dichloromethane.

The organic phases are dried over $MgSO_4$. After evaporation of the solvent, the oil is chromatographed on a silica column (eluant:PE/AcOEt 7/3).

Melting Point:130–131° C.

Step D: 7-Hydroxy-2,3-dihydro-1,4-benzodioxin-6-carbaldehyde 4 eq. of $AlCl_3$ are suspended in 10 ml of anhydrous $CH_2Cl_2$. Under an inert atmosphere, 100 mg (5.55 mmol) of the compound obtained in Step C, dissolved in 10 ml of anhydrous $CH_2Cl_2$, are added to that mixture and allowed to act for 2 hours at ambient temperature. The mixture is hydrolysed with an ice-cold 2N HCl solution; the solution is then extracted with $CH_2Cl_2$ and dried over $MgSO_4$. After evaporation of the solvent, purification on a silica column (eluant:PE/AcOEt 7/3) is carried out and the pure product is isolated.

Melting point: 114–115° C.

PREPARATION 2

9-Methoxy-3H-benzo[f]chromene-2-carbonitrile

Step A: 2,7-Dimethoxynaphthalene

Methylation of 2,7-dihydroxynaphthalene (10 g:62.43 mmol) is carried out in acetone (100 ml) in the presence of dimethyl sulphate (12.06 ml:127 mmol:2.03 eq.) and dry potassium carbon-ate (42.3 g:306 mmol:4.9 eq.). The temperature of the reaction medium is 56° C. for 6 hours and then 40° C. for 12 hours. Hydrolysis (7.4 ml of water) requires 2 hours of stirring at ambient temperature. After filtering off the salts over Celite and concentrating the remaining filtrate, extraction with dichloromethane yields an organic phase, which, after evaporation, has the appearance of a beige solid. The latter is rendered colourless using active carbon and then recrystallised from a $PE/CH_2Cl_2$ mixture.

Melting point: 138° C.

Step B: 2,7-Dimethoxy-1-naphthaldehyde

Titanium tetrachloride (4.09 ml:37.5 mmol:1.4 eq.) and αα-dichloromethyl methyl ether (3.6 ml:37.5 mmol:1.5 eq.), previously dissolved in 14 ml of dichloromethane, are injected in succession into a solution of the compound obtained in Step A (5 g:26.3 mmol) in anhydrous dichloromethane (50 ml). After those operations have been carried out at 0° C., the temperature is gradually returned to 25° C. and that temperature is then maintained for 5 hours. The reaction mixture is then slowly poured onto ice, and a 3N hydrochloric acid solution (103 ml) is subsequently added with caution. After hydrolysis of the complex, the product is extracted with dichloromethane, washed with water and then with a saturated solution of sodium hydrogen carbonate. The dry residue recovered after concentration is washed with diethyl ether, thereby allowing isolation of the pure aldehyde.

Melting point: 94° C.

Step C: 2-Hydroxy-7-methoxy-1-naphthaldehyde

After the dimethoxylated product obtained in Step B (2 g:9.25 mmol) has been dissolved in anhydrous dichloromethane, 97% BBr$_3$Me$_2$S complex (2.98 g:9.25 mmol:1 eq.) is introduced at ambient temperature. After 35 minutes of stirring, hydrolysis is carried out with a saturated solution of sodium hydrogen carbonate (pH=8). The product is extracted with dichloromethane and then purified on a silica column AcOEt/PE (3/7).

Melting point: 126° C.

Step D: 9-Methoxy-3H-benzo[f]chromene-2-carbonitrile

Under an anhydrous atmosphere, the aldehyde obtained in Step C (2 g:9.9 mmol) is partially solubilized in acrylonitrile (6.5 ml:49.4 mmol:10 eq.). The solution becomes clear after the addition of 1,4-diazabicyclo[2.2.2]octane (227 mg:2.47 mmol:0.25 eq.) and becomes a red colour when heated at reflux for a period of 18 hours. The reaction medium is then diluted with ethyl acetate and washed in succession with a 1N sodium hydroxide solution (20 ml) and then a 1N hydrochloric acid solution (20 ml). The concentrated organic phases are purified on a flash silica column eluted with an AcOEt/PE mixture (0.1/1).

Melting point: 134° C.

PREPARATION 3

2,3-Dihydro-1,4-benzodioxin-2-carbonitrile 1.45 g (15.5 mmol) of 2-chloroacrylonitrile and 6 g (43.5 mmol) of dry potassium carbonate are added in succession to 6.6 g (60 mmol) of catechol dissolved in 80 ml of anhydrous acetone. The operation is repeated 4 times within one hour; the mixture is then heated to boiling. After 18 hours at reflux under argon, the reaction mixture is cooled and then filtered over Celite. After evaporation of the solvent, the residue is taken up in a water/ethyl acetate mixture (50:50) and then the aqueous phase is extracted with ethyl acetate. The organic phase, dried over magnesium sulphate and then filtered, is evaporated under reduced pressure. The title nitrile is obtained pure in the form of a white solid after purification on a silica column (eluant:AcOEt/PE 30/70).

Melting point: 58° C.

PREPARATION 4

Ethyl 2,3-dihydro-1,4-benzodioxin-2-carboxylate 26 g (100 mmol) of ethyl 2,3-dibromopropionate and 36.4 g (264 mmol) of anhydrous potassium carbonate are added to 40 g (181 mmol) of catechol dissolved in 200 ml of anhydrous acetone. The operation is repeated 4 times within one hour; the reaction mixture is then heated to boiling. After 18 hours at reflux under argon, the mixture is cooled and then filtered over Celite. After concentration of the filtrate in vacuo, the residue is hydrolysed and then the aqueous phase is extracted with ether. The organic phase is dried over magnesium sulphate and then concentrated in vacuo. The title ester is obtained pure by distillation under reduced pressure (15 mm Hg; b.p.=155° C.).

PREPARATION 5

Ethyl 1,4-benzodioxin-2-carboxylate

Step A: Ethyl 2,3-dibromo-2,3-dihydro-1,4-benzodioxin-2-carboxylate 6 g (28.88 mmol) of the 2,3-dihydrobenzodioxin ester obtained in Preparation 4 and 11.25 g (63.38 mmol) of N-bromosuccinimide are added to 100 ml of anhydrous carbon tetrachloride containing a spatula tip of AIBN; the mixture is then heated at reflux under an inert atmosphere for 4 hours. The succinimide formed is then filtered off; the solvent is then evaporated under reduced pressure to yield the dibrominated ester of the title in the form of an orange solid.

Melting point: 92° C.

Step B: Ethyl 1,4-benzodioxin-2-carboxylate 12 g (32.78 mmol) of the dibrominated compound obtained in Step A are dissolved in 60 ml of anhydrous acetone; 18 g (120 mmol) of sodium iodide are then added to the solution. After 4 hours of stirring at ambient temperature and under argon, the solvent is evaporated in vacuo and the residue is then taken up in water. The aqueous phase is then extracted with ethyl acetate; the organic phase is then rendered colourless using a saturated solution of sodium thiosulphate. After drying over magnesium sulphate and filtration, the solvent is evaporated under reduced pressure. The residue obtained is purified on a silica column (eluant:AcOEt/PE 30/70) to yield the title ester in the form of a chestnut-brown solid.

Melting point: 42° C.

PREPARATION 6

Ethyl 7-acetyloxy-2,3-dihydro-1,4-benzodioxin-2-carboxylate

Step A: Ethyl (6 and 7)-acetyl-2,3-dihydro-1,4-benzodioxin-2-carboxylate 9 g (115.4 mmol) of acetyl chloride are added to a solution of 16 g (77 mmol) of the ester obtained in Preparation 4 in 120 ml of anhydrous carbon disulphide. The temperature is lowered to 0° C.; 25.70 g (192.8 mmol) of aluminium chloride are then added very slowly to the reaction medium. After 4 hours of stirring under an inert atmosphere, the mixture is hydrolysed with an ice-cold 2N hydrochloric acid solution and then extracted with dichloromethane. The organic phase is then washed with a saturated solution of sodium hydrogen carbonate and then dried over magnesium sulphate. After evaporation of the solvent in vacuo, the two title esters are obtained in the form of a yellow oil after passage over a silica column (eluant:Et$_2$O/PE:40/60).

Step B: 7-Acetyl-2,3-dihydro-1,4-benzodioxin-2-carboxamide 16 g (75.4 mmol) of the mixture of the two esters obtained in Step A are dissolved in 150 ml of an ethanol/water mixture (3:1). After addition of 50 ml of a 28% solution of ammonia, the reaction medium is stirred for 3 days at ambient temperature. The title amide precipitates from the medium whereas the isomer acylated in the 6-position remains in solution. After filtering off the precipitate and washing several times with ethanol, the solid obtained is recrystallised twice or three times from a water/ethanol mixture (70/30).

Melting point: 220° C.

Step C: Ethyl 7-acetyl-2,3-dihydro-1,4-benzodioxin-2-carboxylate 150 ml of ethanol are saturated with hydrochloric acid; 6 g (27.12 mmol) of the amide obtained in Step B are then added to the medium. After 18 hours of reflux, the mixture is cooled and then filtered. The filtrate is concentrated in vacuo and the residue is taken up in water; the aqueous phase is then neutralised with solid sodium hydrogen carbonate. After extraction with dichloromethane, the organic phase is dried over magnesium sulphate, filtered and then concentrated in vacuo. The title ester is obtained in the form of a white solid after passage over a silica column (eluant:AcOEt/PE:30/70).

Melting point: 57° C.

Step D: Ethyl 7-acetyloxy-2,3-dihydro-1,4-benzodioxin-2-carboxylate 4 g (16 mmol) of the ester obtained in Step C are dissolved in 60 ml of anhydrous dichloromethane; 6.1 g (35.4 mmol) of meta-chloroperbenzoic acid are then added to the medium. After 18 hours of reflux under an inert atmosphere, the mixture is cooled and then hydrolysed with ice-cold water. The aqueous phase is extracted with dichloromethane; the organic phase is then washed several times with a saturated solution of sodium hydrogen carbonate. After drying over magnesium sulphate and evaporation of the solvent in vacuo, the residue obtained is purified on a silica column (eluant:AcOEt/PE:30/70) to yield the title ester in the form of a syrup.

PREPARATION 7

2-(1,4-Benzodioxin-2-yl)-1-ethanamine

Step A: 2-Bromo-1,4-benzodioxin

A solution of 6 g (44.1 mmol) of 2,3-dihydro-1,4-benzodioxin and 18.8 g (105.6 mmol) of N-bromosuccinimide in 80 ml of anhydrous carbon tetrachloride is heated at reflux under an inert atmosphere after having added a spatula tip of AIBN. After 2 hours, the succinimide formed is filtered off, the solvent is then evaporated in vacuo. The crude dibrominated product is then taken up in 90 ml of anhydrous ether; 9.9 g (88.2 mmol) of potassium tert-butylate are then slowly added to that solution. After 8 hours of stirring under argon and at ambient temperature, the salts are filtered off over Celite; the solvent is then evaporated in vacuo. The title brominated product is obtained pure in the form of a clear oil after passage over a silica column (eluant:PE).

Step B: 2-(1,4-Benzodioxin-2-yl)-1-ethanol 3.73 g (17.5 mmol) of the compound obtained in Step A are dissolved in 90 ml of anhydrous tetrahydrofuran; the mixture is then cooled to −78° C. 16.4 ml (26.25 mmol) of n-butyllithium (1.6 M/hexane) are then slowly added to the solution; the reaction mixture is then stirred for 2 hours under argon at the same temperature. 2.2 ml (17.5 mmol) of boron trifluoride etherate and an excess of ethylene oxide are added in succession to the solution. After 30 minutes of stirring at −78° C., the reaction mixture is hydrolysed with a saturated ammonium chloride solution; the aqueous phase is then extracted with ethyl acetate. The organic phase, dried over magnesium sulphate and then filtered, is concentrated in vacuo. The title alcohol is obtained pure in the form of a clear oil after passage over a silica column (eluant:AcOEt/PE:20/80).

Step C: 2-(1,4-Benzodioxin-2-yl)ethyl 4-methyl-1-benzenesulphonate 2.27 g (12.77 mmol) of the alcohol obtained in Step B are dissolved in 50 ml of anhydrous dichloromethane. 3.65 g (18.35 mmol) of tosyl chloride and 5.3 ml (38.1 mmol) of triethylamine are added in succession to the medium; the solution is then stirred for 18 hours at ambient temperature and under an inert atmosphere. After evaporation of the solvent in vacuo, the title tosylate is obtained pure in the form of a white solid after passage over a silica column (eluant:AcOEt/PE:15/85) in a quantitative yield.

Melting point:103–105° C.

Step D: 2-(2-Iodoethyl)-1,4-benzodioxin 1.33 g (4 mmol) of the tosylate obtained in Step C are dissolved in 50 ml of anhydrous acetone. 1.2 g (8 mmol) of sodium iodide are then added to the medium; the solution is then heated at reflux for 3 hours under argon. After cooling of the mixture, the solvent is evaporated in vacuo; the residue is then taken up in water. The aqueous phase is extracted with dichloromethane. The organic phase, dried over magnesium sulphate and then filtered, is concentrated in vacuo. The iodinated compound is obtained pure in the form of a clear oil after passage over a silica column (eluant:AcOEt/PE:20/80).

Step E: 2-[2-(1,4-Benzodioxin-2-yl)ethyl]-1,3-isoindolinedione 1 g (3.47 mmol) of the iodinated compound obtained in Step D and 0.964 g (5.2 mmol) of potassium phthalimide are dissolved in 20 ml of anhydrous N,N-dimethylformamide; the reaction mixture is then heated at 60° C. for 22 hours under argon. After cooling of the mixture, the solvent is evaporated in vacuo; the residue is then taken up in ethyl acetate. After washing with water and extraction of the aqueous phase with ethyl acetate, the organic phases are dried over magnesium sulphate. The solvent is then evaporated in vacuo; the title phthalimide is then obtained pure in the form of a white solid after passage over a silica column (eluant:AcOEt/PE:30/70).

Melting point: 122–123° C.

Step F: 2-(1,4-Benzodioxin-2-yl)-1-ethanamine 0.837 g (2.37 mmol) of the phthalimide obtained in Step E and 0.358 g (7.16 mmol) of hydrazine monohydrate are dissolved in 20 ml of tetrahydrofuran; the mixture is then heated at reflux for 5 hours. After filtering off the solid, the filtrate is concentrated in vacuo; the residue is then taken up in dichloromethane and dried over magnesium sulphate. The filtered organic phase is concentrated in vacuo to yield the amine in the form of a yellow oil.

PREPARATION 8

Ethyl 2-[7-methoxy-1,4-benzodioxin-2-yl]acetate

Step A: Ethyl 2-[7-(acetyloxy)-1,4-benzodioxin-2-yl]acetate 6 g (22.6 mmol) of the ester obtained in Preparation 6 are dissolved in 120 ml of anhydrous carbon tetrachloride; 8.8 g (49.6 mmol) of N-bromosuccinimide are then added to the medium. After having added a spatula tip of AIBN, the reaction mixture is heated at reflux for 6 hours under an inert atmosphere. The succinimide formed is then filtered off; the filtrate is then concentrated in vacuo to yield the dibrominated product quantitatively. 10 g (23.6 mmol) of the dibrominated product and 14.4 g (82.6 mmol) of sodium iodide, dissolved in 170 ml of anhydrous acetone, are stirred for 4 hours under an inert atmosphere. After evaporation of the solvent in vacuo, the residue is taken up in water; the aqueous phase is then extracted with ethyl acetate. The organic phase is rendered colourless using a saturated solution of sodium thiosulphate. After drying over magnesium sulphate and evaporation of the solvent in vacuo, the residue obtained is purified on a silica column (eluant:AcOEt/PE:30/70) to yield the title ester in the form of a white solid.

Melting point: 66° C.

Step B: Ethyl 2-[7-hydroxy-1,4-benzodioxin-2-yl]acetate 0.84 g (3.78 mmol) of the ester obtained in Step A is dissolved in 20 ml of anhydrous ethanol; the medium is then adjusted to a basic pH using a molar solution of sodium ethanolate (0.5 ml). After 18 hours of stirring under an inert atmosphere and at ambient temperature, the reaction mixture is neutralised with DOWEX X-8 resin (acid form). The solid is then filtered off; the filtrate is then concentrated in vacuo. The residue obtained is purified on a silica column (eluant:AcOEt/PE:50/50) to yield the title compound in the form of a white solid.

Melting point: 160° C.

Step C: Ethyl 2-[7-methoxy-1,4-benzodioxin-2-yl]acetate 2.8 g (12.75 mmol) of the ester obtained in Step B are dissolved in 30 ml of anhydrous N,N-dimethylformamide.

0.61 g (16 mmol) of sodium hydride is then added slowly to the reaction mixture previously cooled to 0° C. After 30 minutes of stirring under argon and at 0° C., 2.28 g (16 mmol) of iodomethane are added to the reaction medium. After 4 hours of stirring at ambient temperature, the solvent is evaporated in vacuo; the residue obtained is then taken up in water and then extracted with ethyl acetate. The organic phase, dried over magnesium sulphate and then filtered, is concentrated under reduced pressure. The title ester is obtained pure in the form of a white solid after passage over a silica column (eluant:ethyl acetate/petroleum ether:30/70).

Melting point: 64° C.

PREPARATION 9

Methyl 3-phenyl-1,4-benzodioxin-2-carboxylate

Step A: 1,4-Benzodioxin-2-carboxylic acid 4 g (19.4 mmol) of the ester obtained in Preparation 5 are dissolved in 70 ml of ethanol; the solution is then cooled to 0° C. 30 ml of a 15% sodium hydroxide solution are slowly added to the medium. After 30 minutes of stirring at 0° C., the solvent is evaporated in vacuo; the residue is then acidified with a hydrochloric acid solution (1N). The aqueous phase is extracted with ethyl acetate; the organic phase is then dried over magnesium sulphate. Evaporation of the solvent in vacuo yields the title acid in the form of a brown solid.

Melting point: 183–184° C.

Step B: Methyl 3-(1,1,1-tributylstannyl)-1,4-benzodioxin-2-carboxylate

A solution of 32.5 ml (65 mmol) of lithium diisopropylamide (2M/heptane) in 40 ml of anhydrous THF is cooled to −78° C. 3.3 g (18.5 mmol) of the acid obtained in Step A, dissolved in 20 ml of anhydrous THF, are slowly added to the medium. After 5 hours of stirring at −78° C., 19.6 ml (65 mmol) of tributyltin chloride are added to the medium. After 1 hour, hydrolysis with a saturated solution of arnmonium chloride is carried out; the aqueous phase is then extracted with ethyl acetate. The organic phase is dried over magnesium sulphate and then concentrated in vacuo. The stannylated acid so formed is dissolved in 40 ml of N,N-dimethylacetamide; 14.31 g (170 mmol) of sodium hydrogen carbonate and also 5.31 ml (85 mmol) of iodomethane are then added to that solution. The reaction medium is then stirred for 40 hours under argon and with protection from light. After evaporation of the solvent in vacuo, the residue is taken up in water; the aqueous phase is then extracted with dichloromethane. The organic phase, dried over magnesium sulphate and then filtered, is concentrated under reduced pressure. The stannylated ester of the title is then purified by passage over a silica column (eluant:AcOEt/CH$_2$Cl$_2$/PE:2.5/2.5/95).

Step C: Methyl 3-phenyl-1,4-benzodioxin-2-carboxylate 9.4 g (19.3 mmol) of the stannylated ester obtained in Step B are dissolved in 70 ml of 1,4-dioxane; 0.74 g (0.69 mmol) of tetrakis(triphenylphosphine)palladium, 5.9 g (28.9 mmol) o iodobenzene and 0.26 g (1.38 mmol) of cuprous iodide are then added in succession to the medium. The reaction mixture is then heated at reflux for 2 hours under an inert atmosphere. After filtering off the remaining catalyst over Celite, the filtrate is concentrated under reduced pressure. The residue obtained is purified on a silica column (eluant:AcOEt/CH$_2$Cl$_2$/PE:2.5/2.5/95) to yield the title ester in the form of a brown solid in an overall yield of 67% for the 3 final Steps.

Melting point: 73° C.

PREPARATION 10

Methyl 7-methoxy-3-phenyl-1,4-benzodioxin-2-carboxylate

Step A: 7-Methoxy-1,4-benzodioxin-2-carboxylic acid 3 g (12.7 mmol) of the ester obtained in Preparation 8 are dissolved in 40 ml of a 3:1 mixture of ethanol/tetrahydrofuran; the solution is then cooled to 0° C. The medium is then made alkaline with an 8% sodium hydroxide solution; stirring is then maintained for 30 minutes more at 0° C. After evaporation of the solvents under reduced pressure, the aqueous phase is extracted with ethyl acetate. The organic phase, dried over magnesium sulphate and then filtered, is concentrated in vacuo to yield the title acid in the form of a white solid.

Melting point: 197° C.

Step B: Methyl 7-methoxy-3-(1,1,1-tributylstannyl)-1,4-benzodioxin-2-carboxylate The acid obtained in Step A is stannylated according to the same procedure as in Step B of Preparation 9. 3.67 g (7.40 mmol) of the resulting crude stannylated acid are dissolved in 25 ml of N,N-dimethylacetamide; 2.3 ml (37 mmol) of iodomethane and 6.21 g (74 mmol) of sodium hydrogen carbonate are then added in succession to the medium. After 4 days of stirring at ambient temperature with protection from light, the solvent is evaporated under reduced pressure; the residue obtained is then taken up in water. The aqueous phase is extracted with dichloromethane. The organic phase, dried over magnesium sulphate and then filtered, is concentrated in vacuo. Chromatography on silica gel (eluant:AcOEtPE:2.5/97.5) yields the title ester in the form of a clear oil.

Step C: Methyl 7-methoxy-3-phenyl-1,4-benzodioxin-2-carboxylate 0.244 g (0.22 mmol) of tetrakis(triphenylphosphine) palladium and 0.084 g (0.44 mmol) of cuprous iodide are added to a solution of 2.15 g (4.36 mmol) of the ester obtained in Step B and of 1.33 g (6.54 mmol) of iodobenzene in 25 ml of 1,4-dioxane. The reaction mixture is then heated at reflux under an inert atmosphere for 2 hours and then allowed to cool. After filtering off the remaining catalyst over Celite, the solvent is evaporated in vacuo. The residue obtained is purified on a silica column (eluant:AcOEt/PE:15/85) to yield the title ester in the form of an oil which crystallises slowly.

Melting point: 82–83° C.

PREPARATION 11

6-Methoxy-2H-3-chromenecarbonitrile

A solution of 0.61 g (4 mmol) of 2-hydroxy-5-methoxybenzaldehyde and 0.112 g (1 mmol) of 1,4-diazabicyclo[2.2.2]octane in 18 ml of acrylonitrile is heated at reflux for 24 hours under argon. After cooling, the medium is diluted with chloroform and then washed with a saturated solution of sodium hydrogen carbonate. The organic phase is then acidified with a hydrochloric acid solution (1N); the aqueous phase is then extracted with chloroform. The organic phases, dried over magnesium sulphate and then filtered, are concentrated under reduced pressure. The title nitrile is obtained pure in the form of a yellow solid after passage over a silica column (eluant:AcOEt/PE:25/75).

Melting point: 70–71° C.

PREPARATION 12

(6-Methoxy-2H-3-chromenyl)methanol

Step A: 6-Methoxy-2H-3-chromenecarboxylic acid 3.18 g (17 mmol) of nitrile obtained in Preparation 11 are added to 50 ml of a 10% sodium hydroxide solution; the reaction mixture is then heated at reflux for 4 hours. After cooling of the mixture, the solvent is evaporated in vacuo; the residue obtained is then acidified with a hydrochloric acid solution (1N). The aqueous phase is then extracted with ethyl acetate; the organic phase is then dried over magnesium sulphate. Evaporation of the solvent under reduced pressure yields the pure title acid in the form of a yellow solid.

Melting point: 199° C.

Step B: (6-Methoxy-2H-3-chromenyl)methanol

A solution of 2.5 g (12.13 mmol) of the acid obtained in Step A in 30 ml of anhydrous tetrahydrofuran is cooled to −16° C.; 2.5 ml (18.2 mmol) of triethylamine are then added dropwise to the medium. After 10 minutes of stirring, 1.98 g (18.2 mmol) of ethyl chloroformate are slowly added to the reaction mixture. The solution is stirred under argon for 3 hours, the salts are filtered off and then the filtrate is cooled to −16° C. 1.84 g (48.5 mmol) of sodium borohydride are added to the medium all at once; 10 ml of methanol are then added very slowly to the solution. After 2 hours of stirring at −16° C., the reaction mixture is hydrolysed with a saturated solution of ammonium chloride; the aqueous phase is then extracted with ethyl acetate. The organic phase, dried over magnesium sulphate and then filtered, is concentrated under reduced pressure. The allyl alcohol of the title is obtained pure in the form of a yellow oil after passage over a silica column (eluant:AcOEt/PE:30/70 then 50/50).

PREPARATION 13

2,3-Dihydro-8H-[1,4]dioxino[2,3-f]chromen-9-yl-methylamine

Step A: 6-(Tetrahydro-2H-2-pyranyloxy)-2,3-dihydro-1,4-benzodioxin-5-carbaldehyde A solution of 7.5 g (31.8 mmol) of the compound obtained in Step A of Preparation 1, protected at the dihydropyran, in 70 ml of anhydrous tetrahydrofuran is cooled to −50° C.; 60 ml (95.4 mmol) of a solution of n-butyllithium (1.6 M/hexane) are then slowly added to the medium. After 2 hours of stirring at that temperature, 10.7 ml (159 mmol) of DMF are slowly added to the solution; stirring is then maintained for 1 hour more at −50° C. After returning to ambient temperature, the reaction mixture is hydrolysed with water and then extracted with ethyl acetate. The organic phase is dried over magnesium sulphate and then concentrated in vacuo. The residue obtained is passed over a silica column (eluant:ethyl acetate/petroleum ether 10/90 then 25/75) to yield the title aldehyde in the form of yellow crystals.

Melting point: 84° C.

Step B: 6-Hydroxy-2,3-dihydro-1,4-benzodioxin-5-carbaldehyde 5 g (18.9 mmol) of the aldehyde obtained in Step A are dissolved in 50 ml of aqueous methanol (90%); 10 ml of a 5% aqueous solution of oxalic acid are then added to the medium. After 3 hours of stirring at ambient temperature, the solvent is evaporated in vacuo; the residue is then taken up in dichloromethane and then washed with a saturated solution of sodium hydrogen carbonate. The organic phase is dried over magnesium sulphate and then concentrated in vacuo. Chromatography on a silica column (eluant:ethyl acetate/petroleum ether:10/90) allows the title compound to be obtained in the form of white crystals.

Melting point: 62–63° C.

Step C: 2,3-Dihydro-8H-[1,4]dioxino[2,3-f]chromene-9-carbaldehyde 3 g (16.6 mmol) of the compound obtained in Step B and 1.4 g (25 mmol) of acrolein are added to a suspension of 3.48 g (25 mmol) of potassium carbonate in 40 ml of 1,4-dioxane; the medium is then heated at reflux under argon for 3 hours. After cooling and filtering off the salts, the solvent is evaporated in vacuo. The residue obtained is taken up in dichloromethane and then washed with water. The organic phase is dried over magnesium sulphate and then concentrated in vacuo. Chromatography on a silica column (eluant:ethyl acetate/petroleum ether 10/90) allows the title compound to be obtained in the form of a yellow solid.

Melting point: 124–125° C.

Step D: 2,3-Dihydro-8H-[1,4]dioxino[2,3-f]chromen-9-ylmethanol 2.18 g (10 mmol) of the aldehyde obtained in Step C are dissolved in 25 ml of anhydrous ethanol and then 0.38 g (10 mmol) of sodium borohydride is added to the medium. After 15 minutes of stirring, the solvent is evaporated in vacuo; the residue obtained is then acidified with a 1N hydrochloric acid solution. The aqueous phase is extracted with dichloromethane; the organic phase is then dried over magnesium sulphate and then concentrated under reduced pressure. The crude product is passed over a silica column (eluant:petroleum ether/ethyl acetate:70/30 then 50/50) to yield the title alcohol in the form of a clear syrup.

Step E: 9-(Bromomethyl)-2,3-dihydro-8H-[1,4]dioxino[2,3-f]chromene 3.83 g (9.09 mmol) of dibromotriphenylphosphorane are added to a solution of 2 g (9.09 mmol) of the alcohol obtained in Step D in 25 mmol of acetonitrile. After 15 min of stirring under argon, the solvent is evaporated in vacuo; the residue obtained is then taken up in 50 ml of a mixture of ether/hexane (1/1). The precipitate formed is filtered off and then washed several times with the same mixture. The organic phase is concentrated under reduced pressure to yield the brominated product of the title in the form of a chestnut-brown syrup.

Step F: 2-(2,3-Dihydro-8H-[1,4]dioxino[2,3-f]chromen-9-yl-methyl)-1,3-isoindolinedione 2.36 g (12.75 mmol) of potassium phthalimide and also 0.166 g (1 mmol) of potassium iodide are added to a solution of 2.54 g (8.5 mmol) of the brominated compound obtained in Step E in 20 ml of anhydrous N,N-dimethylformamide; the medium is then stirred under argon for 10 hours. The solvent is evaporated in vacuo; the residue obtained is then taken up in water and extracted with dichloromethane. The organic phase is dried over magnesium sulphate and then concentrated under reduced pressure. Chromatography on a silica column (eluant:ethyl acetate/petroleum ether 10/90) yields the title phthalimide in the form of a white solid.

Melting point: 137° C.

Step G: 2,3-Dihydro-8H-[1,4]dioxino[2,3-f]chromen-9-yl-methylamine 1 g (3.02 mmol) of the phthalimide obtained in Step E is dissolved in 25 ml of tetrahydrofuran. After adding 0.6 g (12 mmol) of hydrazine hydrate, the medium is heated at reflux for 4 hours and then allowed to cool. The solid formed is filtered off; the filtrate is then concentrated in vacuo to yield the title amine in the form of a yellow oil.

PREPARATION 14

9-Methoxy-2,3-dihydro-1H-benzo[f]chromen-1-one

Step A: 3-(7-Methoxy-1,4-dihydro-2-naphthyl)oxypropanenitrile

The procedure is as in Step A of Example 12, starting from 7-methoxy-1,4-dihydro-2-naphthol.

Step B: 9-Methoxy-2,3-dihydro-1H-benzo[f]chromen-1-one

The procedure is as in Steps B and C of Example 12.

PREPARATION 15

9-Methoxy-2,3-dihydro-1H-benzo[f]chromene-1-carbonitrile

In an anhydrous medium, the ketone obtained in Preparation 14 (500 mg, 2.19 mmol), diethylcyanophosphonate (2 eq; 4.38 mmol, 715 µl) and also a 0.5M solution of lithium cyanide in DMF (3 eq; 6.57 mmol, 13.15 ml) are mixed in 20 ml of THF. After 30 minutes of stirring, the reaction mixture is hydrolysed and then extracted with AcOEt. In parallel, a solution of samarium iodide is prepared. The samarium (4.5 eq; 9.86 mmol; 1.48 g) is suspended in 10 ml of THF and then diiodoethane (3 eq; 6.57 mmol; 1.85 g), diluted in 10 ml of THF, is added dropwise. When the samarium iodide solution has become blue, the previously formed complex is dissolved in 5 ml of THF and 0.21 ml of tert-butanol and then added. The solution is stirred for 12 hours at ambient temperature. The reaction mixture is hydrolysed with a 10% HCl solution. After extraction with AcOEt, the organic phase is washed with a 10% solution of $Na_2S_2O_3$ and then twice with a saturated solution of $NaHCO_3$. The residue obtained is purified by flash chromatography on silica gel (eluant:PE/AcOEt (8/2)). The title product is obtained in the form of an oil.

PREPARATION 16

2-(9-Methoxy-2,3-dihydro-1H-benzo[f]chromen-1-yl)acetonitrile

Step A: 2-(9-Methoxy-2,3-dihydro-1H-benzo[f]chromen-1-ylidene)acetonitrile

In an anhydrous medium, diethyl cyanomethylphosphonate (3 eq; 17.1 mmol; 2.76 ml) is added slowly to a suspension of 50% sodium hydride (3 eq; 17.1 mmol; 820 mg) in 50 ml of THF, at 0° C. The reaction medium is stirred for 10 minutes at 0° C. and then cooled to −78° C. The ketone obtained in Preparation 14 (1.3 g; 5.7 mmol), dissolved in 15 ml of THF, is added. The temperature is then slowly returned to 20–25° C. over 2 hours 30. After removal of the solvent, the compound is extracted with AcOEt. The organic phase is washed with a large amount of a saturated solution of NaCl and then concentrated under reduced pressure. The desired product is obtained in the form of a solid.

Melting point: 61–63° C.

Step B: 2-(9-Methoxy-2,3-dihydro-1H-benzo[f]chromen-1-yl)acetonitrile

The unsaturated compound obtained in Step A (1.775 eq; 7.07 mmol.), solubilized in 50 ml of ethanol and a few drops of THF, is introduced into a Parr reactor. 10% palladium-oncabon (266 mg; 15% by weight) is then added. The mixture is left under hydrogen pressure of 45 psi, with stirring, for 18 hours. After filtration over Celite, the solvent is removed under reduced pressure. The residue is purified by flash chromatography on silica gel (eluant:PE/AcOEt (9/1)). The desired product is obtained in the form of a solid.

Melting point: 122–123° C.

PREPARATION 17

6-Methoxy-2-phenyl-4H-4-chromenone

The title product is obtained by condensation in sodium hydride of acetophenone with ethyl 5-methoxy-2-(methoxymethoxy)benzoate, and then the action of HCl in ethanol.

EXAMPLE 1

N-[(3,4-Dihydro-2H-6,7-ethylenedioxy-chromen-3-yl)methyl]acetamide

Step A: 2H-6,7-Ethylenedioxy-chromene-3-carbonitrile 1 g (5.55 mmol) of the compound obtained in Preparation 1, 10 ml of acrylonitrile and 0.150 g (1.2 mmol) of 1,4-diazabicyclo[2.2.2]octane are introduced into a 250 ml flask. The mixture is stirred at 50° C. under an inert atmosphere for 20 h and then cooled. The product is hydrolysed and then extracted with ethyl acetate. The organic phase is dried over $MgSO_4$. The product is purified on a silica column (eluant:PE/AcOEt, 1/1).

Melting point: 146° C.

Step B: 3,4-Dihydro-2H-6,7-ethylenedioxy-chromene-3-carbonitrile 200 mg (0.93 mmol) of the product obtained in Step A are introduced into a Parr hydrogenator apparatus together with 15 ml of ethanol and 20 mg of 10% palladium-on-carbon. The mixture is stirred under a hydrogen atmosphere for 24 h. The mixture is filtered over Celite; the ethanol is then evaporated. The title product is purified on a silica column (eluant:PE/AcOEt, 1/1).

Step C: 3,4-Dihydro-2H-6,7-ethylenedioxy-chromen-3-yl-methylamine 175 mg of the product obtained in Step B are dissolved in 10 ml of distilled ether. 77 mg of $LiAlH_4$ are added to that solution. The mixture is allowed to react for 24 h at ambient temperature. The mixture is then hydrolysed with 0.08 ml of water, 0.08 ml of 15% NaOH and finally 0.25 ml of water. The mixture is filtered over Celite and washed with ethyl acetate, which is evaporated. The title product is purified on a silica column (eluant:$CH_2Cl_2$/MeOH:90/10).

Step D: N-[(3,4-Dihydro-2H-6,7-ethylenedioxy-chromen-3-yl)methyl]acetamide

The product obtained in Step C is dissolved in 5 ml of $CH_2Cl_2$ in a flask. At 0° C. in ice, 0.2 ml of pyridine and 0.2 ml of acetic anhydride are added and allowed to act for 2 h. The product is then hydrolysed and then extracted with dichloromethane. The organic phase, dried over $MgSO_4$, is concentrated and the remaining pyridine is evaporated with toluene. The title product is purified on a silica column (eluant:$CH_2Cl_2$MeOH) and then recrystallised from ethanol and cyclohexane.

| | Melting point: 178° C. Elemental microanalysis: | | |
|---|---|---|---|
| | C | H | N |
| % Calculated | 63.87 | 6.51 | 5.32 |
| % Found | 63.91 | 6.43 | 5.18 |

EXAMPLE 2

N-(3,4-Dihydro-2H-6,7-ethylenedioxy-chromen-3-yl)acetamide

Step A: 3-Nitro-2H-6,7-ethylenedioxychromene

In a three-necked flask equipped with a Dean-Stark and a condenser, 1.3 g (7.216 mmol) of the product obtained in Preparation 1 are dissolved in 30 ml of toluene; 0.5 eq. of di-n-butylamine and 2.2 eq. of phthalic anhydride are added. The mixture is heated at reflux and 4 eq. of 2-nitroethanol are added in four batches. After 20 hours of reaction, the reaction mixture is cooled; the solvent is then evaporated. The crude residue is purified on a silica column (eluant:PE/AcOEt 7/3) and the remaining starting product is removed by washings in a basic medium (10% NaOH), yielding the final compound in the form of orange crystals.

Melting point: 168° C.

Step B: 3-Nitro-3,4-dihydro-2H-6,7-ethylenedioxychromene

In a flask, 1 g (42.52 mmol) of the unsaturated product obtained in Step A is dissolved in 20 ml of $CHCl_3$ and 6 ml of isopropanol. 4 g of silica (270–400 mesh) and 4 eq. of $NaBH_4$ are added together with acetic acid (a few drops). The precipitate is filtered off and rinsed with $CH_2Cl_2$. The solvent is co-evaporated with toluene. Purification of the title product is carried out on a silica column (eluant:PE/AcOEt 7/3). The pure product is obtained in the form of yellow crystals.

Melting point: 150–151° C.

Step C: 3,4-Dihydro-2H-6,7-ethylenedioxy-chromen-3-ylamine

100 mg (0.425 mmol) of the compound obtained in Step B are dissolved in 4 ml of ethanol by heating at 45° C.; 0.05 g of Raney nickel is introduced into the reaction medium; 0.3 ml of 98% hydrazine hydrate is then added in fractions over a period of one hour. Stirring is continued at 45° C. for a further 30 minutes. The reaction medium is allowed to cool and filtered over Celite, and the remaining catalyst is washed with ethanol. After evaporation in vacuo, purification is carried out on a silica column (eluant:$CH_2Cl_2$ then $CH_2Cl_2$/MeOH 95/5 then $CH_2Cl_2$/MeOH 9/1) and the product is obtained in the form of an oil.

Step D: N-(3,4-Dihydro-2H-6,7-ethylenedioxy-chromen-3-yl)acetamide

The compound obtained in Step C (100 mg ; 0.5 mmol) is dissolved in 6 ml of dichloromethane. 0.4 ml of pyridine and 0.3 ml of acetic anhydride are added. The mixture is stirred under an inert atmosphere for 2 hours. The mixture is hydrolysed with water and then extracted with dichloromethane. The solvent is evaporated and the remaining pyridine is co-evaporated with toluene. The product is purified on a silica column (eluant:$CH_2Cl_2$/MeOH:95/5) and recrystallised from cyclohexane and ethanol.

| Melting point: 174–175° C. Elemental microanalysis: | | | |
|---|---|---|---|
| | C | H | N |
| % Calculated | 62.64 | 6.07 | 5.62 |
| % Found | 62.34 | 6.06 | 5.57 |

EXAMPLE 3

N-(3,4-Dihydro-2H-6,7-ethylenedioxy-chromen-3-yl)benzamide

The procedure is as in Example 2, with replacement in Step D of the acetic anhydride with benzoic anhydride.

EXAMPLE 4

N-[(9-Methoxy-2,3-dihydro-1H-benzo[f]chromen-2-yl)methyl]acetamide

Step A: 9-Methoxy-2,3-dihydro-1H-benzo[f]chromene-2-carbonitrile

The same procedure is used as in Step B of Example 1, starting from the compound obtained in Preparation 2.

Step B: N-[(9-Methoxy-2,3-dihydro-1H-benzo[f]chromen-2-yl)methyl]acetamide

The same procedure is used as in Steps C and D of Example 1, starting from the compound obtained in Step A.

| Melting point: 138° C. Elemental microanalysis: | | | |
|---|---|---|---|
| | C | H | N |
| % Calculated | 71.56 | 6.71 | 4.91 |
| % Found | 71.50 | 6.79 | 4.86 |

EXAMPLE 5

N-(9-Methoxy-2,3-dihydro-1H-benzo[f]chromen-2-yl)acetamide

Step A: 9-Methoxy-3H-benzo[f]chromene-2-carboxylic acid

A mixture of the cyano compound obtained in Preparation 2 (1 g:4.21 mmol) and a 10% sodium hydroxide solution (34 ml:84.3 mmol:20 eq.) is heated at reflux for 5 hours. The cooled reaction medium is extracted at a basic pH with ethyl acetate. Precipitation of the acid is performed in the cold state by acidification of the remaining aqueous phase with 2N, and then 3N, hydrochloric acid. The solid recovered by filtration is dried in vacuo in the presence of phosphorus pentoxide.

Melting point: 226° C.

Step B: 9-Methoxy-2,3-dihydro-1H-benzo[f]chromene-2-carboxylic acid

The unsaturated acid obtained in Step A (750 mg:2.9 mmol) is solubilized in a mixture of ethanol/dimethylformamide (20 ml:3 ml) in the reactor of a Parr apparatus. After addition of the catalyst, 10% palladium-on-carbon (75 mg; 10% by weight), the whole is stirred at ambient temperature at a pressure of 45 psi for 4 hours. The solvents are removed; the residual oil is then precipitated and washed with diethyl ether.

Melting point: 165° C.

Step C: N-(9-Methoxy-2,3-dihydro-1H-benzo[f]chromen-2-yl)acetamide

After dissolving the acid obtained in Step B (50 mg:0.19 mmol) in acetone (2 ml) under an inert atmosphere, distilled triethylamine (0.07 ml:0.52 mmol:2.7 eq.) and also distilled ethyl chloroformate (0.06 ml:0.68 mmol:3.5 eq.) are slowly introduced in succession at 0° C. After 30 minutes of stirring, sodium azide (57 mg:0.87 mmol:4.5 eq.), dissolved in 1 ml of water, is added. After a similar amount of time has passed, the reaction medium is extracted with dichloromethane. The resulting organic phase is concentrated, taken up in I ml of toluene and heated at reflux for 30 minutes. While in the hot state, glacial acetic acid (1 ml) is then introduced; the heating is then continued for 1 hour 30 minutes. At ambient temperature, the products are extracted with ethyl acetate and then purified on a flash silica column $CHCl_3$/AcOEt 7/3. The title compound is washed with diethyl ether.

|  | C | H | N |
|---|---|---|---|
| % Calculated | 70.83 | 6.32 | 5.16 |
| % Found | 70.75 | 6.29 | 4.95 |

Melting point: 186° C.
Elemental microanalysis:

EXAMPLE 6

N-[(9-Methoxy-2,3-dihydro-1H-benzo[f]chromen-2-yl)methyl]-2-cyclopropylacetamide The title compound is obtained by the same procedure as for Example 4, with replacement in the final Step of acetic anhydride with cyclopropanecarboxylic anhydride.

EXAMPLE 7

N-[(9-Methoxy-2,3-dihydro-1H-benzo[f]chromen-2-yl)methyl]-1-cyclohexyl carboxamide The title example is obtained as in Example 5, using cyclohexanecarboxylic acid instead of acetic acid.

EXAMPLE 8

N-Methyl-9-methoxy-2,3-dihydro-1H-benzo[f]chromene-2-carboxamide

Methylamine, condensed with the acid obtained in Step B of Example 5, allows the title compound to be obtained.

EXAMPLE 9

N-Methyl-9-methoxy-3H-benzo[f]chromene-2-carboxamide

Methylamine, condensed with the compound obtained in Step A of Example 5, yields the title compound.

EXAMPLE 10

N-[2-(3,4-Dihydro-2H-4-chromenyl)ethyl]acetamide
Step A: 2-(3,4-Dihydro-2H-4-chromenylidene)acetonitrile Diethyl cyanomethylphosphonate (1.15 eq.) is slowly added to a suspension of sodium hydride (1.15 eq.) in anhydrous tetrahydrofuran at 0° C. The reaction medium is stirred for 10 minutes at 0° C. and then cooled to −78° C. 4-Chromanone dissolved in tetrahydrofuran is added. The temperature is then returned slowly to 20–25° C. over 2 hours 30. After removal of the solvent, the compounds are extracted with ethyl acetate. The organic phase is washed with a large amount of a saturated solution of sodium chloride, concentrated and purified (Z/E mixture) on a silica column (AcOEt/PE 3/7).
Step B: 2-(3,4-Dihydro-2H-4-chromenyl)acetonitrile The unsaturated compound obtained in Step A (Z+E mixture), solubilized in ethanol (20 ml), is introduced into the reactor of a Parr apparatus. 10% (by weight) palladium-on-carbon is then added. The double bond is hydrogenated at a pressure of 45 psi for 12 hours.

The catalyst is removed by filtration; the solvent is then evaporated. The residual oil is purified on a silica column eluted by a mixture of AcOEt/PE 3/7. Colourless oil.
Step C: N-[2-(3,4-Dihydro-2H-4-chromenyl)ethyl]acetamide The saturated cyano compound obtained in Step B is solubilized in the reactor of a Parr apparatus with acetic anhydride. Sodium acetate (1.5 eq.) and also Raney nickel (6 mg per 50 mg of product) are then introduced into the reaction medium. The whole is heated at 50° C. under hydrogen pressure of 40 psi for 12 hours. Once the solvent has been removed after returning to normal temperature and pressure conditions, extraction is carried out with ethyl acetate. Purification of the concentrated organic phase by flash chromatography (CHCl$_3$/AcOEt 7/3) results in the desired amide. Colourless gum.

EXAMPLE 11

N-[2-(3,4-Dihydro-2H-4-chromenyl)ethyl]ethanethioacetamide

The compound obtained in Example 10, subjected to Lawesson's reagent, allows the title compound to be obtained.

EXAMPLE 12

N-[2-(6-Methoxy-3,4-dihydro-2H-4-chromenyl)ethyl]acetamide
Step A: 2-(4-Methoxyphenoxy)cyanoethane A mixture of 4-methoxyphenol (10 g:80.5 mmol) and Triton B (2.29 ml:14.5 mmol 0. 18 eq.) in acrylonitrile (50 ml) is heated at reflux for 48 hours. After the solvent has been partially removed, the products are extracted with ethyl acetate and washed with water and then with a 6N hydrochloric acid solution. The residual chestnut-brown oil is purified on a flash silica column eluted with an AcOEt/PE gradient.

Melting point: 58° C. (pale yellow solid)
Step B: 3-(4-Methoxyphenoxy)propanoic acid Hydrolysis of the cyano compound obtained in Step A (3 g:16.93 mmol) is carried out using 37% concentrated hydrochloric acid (8.3 ml:84.3 mmol:5 eq.) at reflux. After dissolution of the starting product, the desired compound precipitates at the end of 2 hours of heating. After the reaction medium has been cooled, the solid is filtered off, washed with an ice-water mixture and introduced into a solution of 10 ml of water containing 1 g of sodium hydrogen carbonate. The latter is stirred vigorously for 1 hour and then filtered. The resulting filtrate yields the pure acid after acidification in the cold state (3N hydrochloric acid) and filtrationMelting Melting point: 104° C. (white solid)
Step C: 6-Methoxy-4-chromanone Cyclisation is carried out on the acid chloride generated starting from the acid. Heating the acid obtained in Step B (500 mg:2.55 mmol) at reflux of toluene (20 ml) for 3 hours in the presence of thionyl chloride (0.56 ml:7.65 mmol:3 eq.) allows easy access to the acid chloride. The solvent and also the excess reagent are removed by concentrating the resulting yellow solution under reduced pressure. The dry residue is then taken up in 20 ml of anhydrous dichloromethane; aluminium chloride (465.9 mg:3.49 mmol:1.5 eq.) is then introduced cautiously. The reaction mixture is hydrolysed in the cold state after 1 hour of stirring at ambient temperature. The product is extracted, washed with water and then purified on a silica column (AcOEt/PE 3/7).

Melting point: 43° C. (pale yellow solid)
Step D: 2-(6-Methoxy-3,4-dihydro-2H-4-chromenylidene)acetonitrile The procedure is as in Step A of Example 10, starting from the compound obtained in Step C.

Step E: 2-(6-Methoxy-3,4-dihydro-2H-4-chromenyl) acetonitrile

The procedure is as in Step B of Example 10, starting from the compound obtained in Step D. Colourless oil.

Step F: N-[2-(6-Methoxy-3,4-dihydro-2H-4-chromenyl) ethyl]acetamide

The procedure is as in Step C of Example 10, starting from the compound obtained in Step E.

Melting point: 138° C.
Elemental microanalysis:

|  | C | H | N |
|---|---|---|---|
| % Calculated | 67.45 | 7.68 | 5.62 |
| % Found | 66.90 | 7.74 | 5.49 |

EXAMPLE 13

N-[2-(6-Methoxy-3,4-dihydro-2H-4-chromenyl) ethyl]butanamide

The cyano compound (500 mg; 2.46 mmol) obtained in Step E of Example 12 is solubilised in a Parr reactor with methanol (50 ml). Raney nickel (6 mg per 50 mg of product) is then added. The mixture is heated at 50° C. under hydrogen pressure of 40 psi for 16 hours. The nickel is then filtered off over Celite and the methanol is evaporated. The crude mixture is dissolved in anhydrous dichloromethane (IO ml); the solution is then cooled to 0° C. Butyryl chloride (1.4 eq.; 3.36 mmol; 348 µl) and then triethylamine (3 eq.; 7.2 mmol; 1.013 ml) are added to the medium. At the end of one hour of stirring, the reaction mixture is acidified with a hydrochloric acid solution (1N). After extraction with dichloromethane, the organic phase is washed with a saturated solution of sodium hydrogen carbonate, dried over magnesium sulphate and then concentrated in vacuo. The residue obtained is purified by flash chromatography with, as eluant:PE/AcOEt (6/4) then (1/1) then (4/6).

The product is obtained in the form of white crystals after washing with ether and pentane.

Melting point: 63–64° C.
Elemental microanalysis:

|  | C | H | N |
|---|---|---|---|
| % Calculated | 69.29 | 8.36 | 5.05 |
| % Found | 69.30 | 8.31 | 5.05 |

EXAMPLE 14

N-[2-(6-Methoxy-3,4-dihydro-2H-4-thiochromenyl) ethyl]acetamide

The procedure is as in Example 12, taking 4-methoxy-benzenethiol as starting product.

EXAMPLE 15

N-[2-(6-Methoxy-3,4-dihydro-2H-4-chromenyl) ethyl]-2-phenylacetamide

The procedure of Steps A, B, C, D and E of Example 12 is followed; reduction of the nitrile is then carried out under the conditions of Step C of Example 1; condensation of phenylacetyl chloride then allows the title compound to be obtained.

EXAMPLE 16

N-[(2,3-Dihydro-1,4-benzodioxin-2-yl)methyl] acetamide 1 g (6.2 mmol) of the nitrile obtained in Preparation 3 is added to a suspension of 0.77 g (9.3 mmol) of sodium acetate and 0.55 g (9.3 mmol) of Raney nickel in 15 ml of acetic anhydride. The reaction medium is subjected to hydrogen pressure of 50 psi at a temperature of 50° C. for 15 hours. After filtering off the salts over Celite, the solvent is evaporated in vacuo. The residue is then taken up in ethyl acetate; the organic phase is then washed with a saturated solution of sodium hydrogen carbonate. After drying over magnesium sulphate and evaporation of the solvent in vacuo, the title amide is obtained pure in the form of a white solid after passage over a silica column (eluant:AcOEt).

Melting point : 86° C.
Elemental microanalysis:

|  | C | H | N |
|---|---|---|---|
| % Calculated | 63.76 | 6.32 | 6.76 |
| % Found | 63.44 | 6.39 | 6.54 |

EXAMPLE 17

N-[(1,4-Benzodioxin-2-yl)methyl]acetamide

Step A: 1,4-Benzodioxin-2-carbonitrile 2 g (12.42 mmol) of the nitrile obtained in Preparation 3, 5.34 g (30 mmol) of N-bromosuccinimide and a spatula tip of AIBN (2,2'-azobis[2-methylpropanenitrile]) in 40 ml of anhydrous carbon tetrachloride are heated at reflux under an inert atmosphere for 6 hours. After cooling the medium and filtering off the succinimide formed, the dibrominated nitrile is obtained pure after evaporation of the solvent in vacuo in a quantitative yield. The dibrominated product and 6.52 g (43.5 mmol) of sodium iodide in 40 ml of anhydrous acetone are stirred for 3 hours at ambient temperature and under an argon atmosphere. The reaction medium is concentrated in vacuo; the residue is then taken up in water. The aqueous phase is then extracted with ethyl acetate; the organic phase is then dried over magnesium sulphate. After evaporation of the solvent in vacuo, the unsaturated nitrile of the title is obtained pure in the form of a white solid after passage over a silica column (eluant:AcOEt/PE:30/70).

Melting point: 86–87° C.

Step B: (1,4-Benzodioxin-2-yl)methanamine 1 g (6.29 mmol) of the nitrile obtained in Step A is dissolved in 50 ml of anhydrous ether; 0.31 g (8.17 mmol) of lithium aluminium hydride is then added very slowly to the solution. After 3 hours of reflux under argon, the reaction medium is returned to ambient temperature and then hydrolysed with, in succession, 0.31 ml of water, 0.31 ml of a 15% sodium hydroxide solution and 0.93 ml of water. After 30 minutes of stirring at ambient temperature, the salts are filtered off; the filtrate is then dried over magnesium sulphate. The filtered organic phase is concentrated in vacuo to yield the title amine in the form of a yellow oil.

Step C: N-[(1,4-Benzodioxin-2-yl)methyl]acetamide

A solution of 0.66 g (4.05 mmol) of the amine obtained in Step B in 5 ml of anhydrous pyridine is cooled to 0° C. 0.46 ml (4.86 mmol) of acetic anhydride is then added to the medium. After 30 minutes of stirring at 0° C. and under argon, the solvent is evaporated in vacuo; the residue is then taken up in dichloromethane. The organic phase is then acidified with a hydrochloric acid solution (1N); the aqueous phase is then extracted with dichloromethane. After drying over magnesium sulphate and filtration, the organic phase is (eluant:petroleum ether/ethyl acetate:70/30 then 50/50) to yield the title alcohol in the passage over a silica column (eluant:AcOEt).

Melting point: 112° C.
Elemental microanalysis:

|  | C | H | N |
|---|---|---|---|
| % Calculated | 64.38 | 5.40 | 6.83 |
| % Found | 64.04 | 5.54 | 6.59 |

EXAMPLE 18

N-[(2,3-Dihydro-1,4-benzodithiin-2-yl)methyl]acetamide

The title compound is obtained in analogous manner to the compound of Example 16, using 1,2-benzenedithiol as starting product.

EXAMPLE 19

N-[(1,4-Benzodithiin-2-yl)methyl]acetamide

The title compound is obtained according to an analogous procedure to the compound of Example 17, taking 1,2-benzenedithiol as starting product.

EXAMPLE 20

N-[3-(2,3-Dihydro-1,4-benzodioxin-2-yl)propyl]acetamide

Step A: (1,4-Benzodioxin-2-yl)methanol 0.342 g (9 mmol) of lithium aluminium hydride is added to a solution of 1.21 g (6 mmol) of the ester obtained in Preparation 5 in 20 ml of anhydrous ether; the medium is then stirred for 30 minutes at ambient temperature and under an inert atmosphere. The reaction mixture is then hydrolysed with, in succession, 0.342 ml of water, 0.342 ml of a 15% sodium hydroxide solution and 1.026 ml of water. After 30 minutes of stirring, the salts are filtered off; the filtrate is then concentrated in vacuo. Chromatography on a silica column (eluant:PE/AcOEt:60/40) results in the title alcohol in the form of an oil which crystallises slowly.

Melting point: 54–55° C.

Step B: 1,4-Benzodioxin-2-carbaldehyde

A solution of 1.2 ml (14 mmol) of oxalyl chloride in 30 ml of anhydrous dichloromethane is cooled to −60° C. under an inert atmosphere; 2 ml (28 mmol) of anhydrous dimethyl sulphoxide are then added to the medium. After 5 minutes of stirring, 1.53 g (9.33 mmol) of the alcohol obtained in Step A in 15 ml of dichloromethane are slowly added to the solution. 15 minutes later, 6.5 ml (47 mmol) of triethylamine are added to the medium. After returning to ambient temperature, the solution is acidified with a hydrochloric acid solution (1N); the aqueous phase is then extracted with dichloromethane. The organic phases, dried over magnesium sulphate and then filtered, are concentrated in vacuo. The title aldehyde is obtained pure in the form of a white solid after passage over a silica column (eluant:AcOEt/PE:10/90).

Melting point: 77–78° C.

Step C: (E)-2-(1,4-Benzodioxin-2-yl)-2-propenenitrile

A suspension of 0.046 g (1.15 mmol at 60% in oil) of sodium hydride in 10 ml of anhydrous tetrahydrofuran is cooled to 0° C.; 0.186 ml (1 mmol) of diethyl cyanomethylphosphonate is then added to the medium. After 10 minutes of stirring under an inert atmosphere, the temperature is lowered to −78° C.; 0.162 g (1 mmol) of the aldehyde obtained in Step B in 10 ml of tetrahydrofuran is then slowly added to the medium. After 3 hours of stirring at that temperature, the mixture is hydrolysed with a saturated solution of sodium hydrogen carbonate; the aqueous phase is then extracted with ethyl acetate. The organic phases, dried over magnesium sulphate and then filtered, are concentrated under reduced pressure. Chromatography on silica gel (eluant:AcOEt/PE:10/90) yields the unsaturated nitrile of the title in the form of a yellow solid.

Melting point: 133° C.

Step D: 3-(2,3-Dihydro-1,4-benzodioxin-2-yl)propanenitrile 0.55 g (2.96 mmol) of the nitrile obtained in Step C is added to a suspension of 0.11 g of 10% palladium-on-carbon in 10 ml of anhydrous ethanol; the mixture is then subjected to hydrogen pressure of 50 psi for 12 hours. The remaining catalyst is filtered off over Celite; the solvent is then evaporated under reduced pressure. The residue obtained is passed over a silica column (eluant:PE/AcOEt:75/25) to yield the title nitrile in the form of a chestnut-brown syrup.

Step E: N-[3-(2,3-Dihydro-1,4-benzodioxin-2-yl)propyl]acetamide 0.53 g (2.82 mmol) of the nitrile obtained in Step D is added to a suspension of 0.25 g (4.23 mmol) of Raney nickel and 0.34 g (4.23 mmol) of sodium acetate in 8 ml of acetic anhydride. The reaction mixture is subjected to hydrogen pressure of 50 psi at 50° C. for 6 hours. The remaining catalyst is then filtered off over Celite; the solvent is then evaporated in vacuo. The residue obtained is taken up in water; the reaction medium is then extracted with ethyl acetate. The organic phase is washed with a saturated solution of sodium hydrogen carbonate and then dried over magnesium sulphate. After filtration and evaporation of the solvent under reduced pressure, the residue obtained is purified on a silica column (eluant:ethyl acetate) to result in the title amide in the form of a clear syrup.

EXAMPLE 21

N-Butyl-3-(2,3-dihydro-1,4-benzodioxin-2-yl)propionamide

After hydrolysis of the nitrile obtained in Step D of Example 20, the title compound is obtained by condensation with N-butylamine in the presence of coupling agents, such as hydroxybenzotriazole or 1-(3-dimethylaminopropyl)-3-ethylcarbodiimide hydrochloride.

EXAMPLE 22

N-[2-(7-Methoxy-2,3-dihydro-1,4-benzodioxin-2-yl)ethyl]acetamide

Step A: (7-Methoxy-2,3-dihydro-1,4-benzodioxin-2-yl)methanol 1.2 g (4.5 mmol) of the ester obtained in Preparation 6 are dissolved in 25 ml of anhydrous ethanol. After addition of 0.5 ml of a molar solution of sodium ethanolate, the reaction medium is stirred for 3 days, under argon and at ambient temperature, and then adjusted to pH 6–7 with DOWEX X-8 resin (acid form). After filtering off the resin and evaporation of the solvent in vacuo, the residue is taken up in 20 ml of N,N-dimethylformamide; the solution is then cooled to 0° C. 0.21 g (5.62 mmol) of 60% sodium hydride in oil is then added slowly to the reaction mixture. After 30 minutes of stirring at 0° C., 0.86 g (6 mmol) of iodomethane is added to the solution. The medium is stirred for 6 hours at ambient temperature; the solvent is then evaporated under reduced pressure. The residue obtained is taken up in water; the aqueous phase is then extracted with ethyl acetate. The organic phase, dried over magnesium sulphate and then filtered, is concentrated under reduced pressure. The residue obtained is reduced using lithium aluminium hydride. The title alcohol is obtained pure in the form of a clear oil after passage over a silica column (eluant:AcOEt/PE:30/70 then 50/50).

Step B: [(7-Methoxy-2,3-dihydro-1,4-benzodioxin-2-yl)methyl]4-methyl-1-benzeneulphonate 2.67 g (13.6 mmol) of the alcohol obtained in Step A and 3.88 g (20.35 mmol) of tosyl chloride are dissolved in 40 ml of anhydrous dichloromethane; 5.7 ml (41 mmol) of triethylamine are then added to that solution. The medium is stirred for 22 h under argon and at ambient temperature; the solvent is then evaporated in vacuo. The title tosylate is obtained pure in the form of a white solid after chromatography on silica gel (eluant:AcOEt/PE:15/85).

Melting point: 89° C.

Step C: 2-(Iodomethyl)-7-methoxy-2,3-dihydro-1,4-benzodioxin 4.67 g (13.36 mmol) of the tosylate obtained in Step B and 4 g (26.7 mmol) of sodium iodide are dissolved in 60 ml of anhydrous acetone; the reaction mixture is then heated at reflux for 48 hours under argon. After cooling of the mixture and evaporation of the solvent in vacuo, the iodinated compound of the title is obtained pure in the form of a clear oil after passage over a silica column (eluant:AcOEt/PE:25/75).

Step D: 2-(7-Methoxy-2,3-dihydro-1,4-benzodioxin-2-yl)acetonitrile 1.35 g (4.43 mmol) of the iodinated compound obtained in Step C and 1.37 g (26.6 mmol) of potassium cyanide are dissolved in 15 ml of anhydrous hexamethylphosphoric triamide; the reaction mixture is then stirred for 2 days under argon and at ambient temperature. The solution is then hydrolysed with a solution of sodium hydrogen carbonate; the aqueous phase is then extracted with dichloromethane. The organic phase, dried over magnesium sulphate acid then filtered, is concentrated under reduced pressure. The title nitrile is obtained pure in the form of a clear oil after chromatography on silica gel (eluant:PE then AcOEt/PE:15/85).

Step E: N-[2-(7-Methoxy-2,3-dihydro-1,4-benzodioxin-2-yl)ethyl]acetamide 0.52 g (2.5 mmol) of the nitrile obtained in Step D and 0.31 g (3.75 mmol) of sodium acetate are dissolved in 15 ml of acetic anhydride. 0.22 g (3.75 mmol) of Raney nickel previously washed in ethanol and then in acetic anhydride is then added to the solution and the medium is then heated at 50° C. under a hydrogen atmosphere (1 atm) for 22 hours. After filtering off the salts, the filtrate is concentrated under reduced pressure; the residue obtained is then taken up in ethyl acetate. The organic phase is washed with a saturated solution of sodium hydrogen carbonate and then dried over magnesium sulphate. The solvent is then evaporated in vacuo. The title amide is obtained pure in the form of a clear syrup after passage over a silica column (eluant:MeOH/$CH_2Cl_2$:2.5/97.5 then 10/90).

EXAMPLE 23

N-Phenyl-2-(7-methoxy-2,3-dihydro-1,4-benzodioxin-2-yl)acetamide

The title compound is obtained after hydrolysis of the nitrile obtained in Step D of Example 22 and then condensation with aniline, in the presence of coupling agents, such as hydroxybenzotriazole or 1-(3-dimethylaminopropyl)-3-ethylcarbodiimide hydrochloride.

EXAMPLE 24

N-[(7-Methoxy-1,4-benzodioxin-2-yl)methyl]acetamide

Step A: 7-Methoxy-1,4-benzodioxin-2-carboxamide 2.9 g (12.35 mmol) of the compound obtained in Preparation 8 are dissolved in 50 ml of ethanol; 50 ml of a 28% solution of ammonia are then added to the reaction medium. After 40 hours of stirring at ambient temperature, the solvents are evaporated in vacuo; the title amide is then obtained pure in the form of a white solid after passage over a silica column (eluant:MeOH/$CH_2Cl_2$: 10/90).

Melting point: 176° C.

Step B: 7-Methoxy-1,4benzodioxin-2-carbonitrile 1.76 g (8.52 mmol) of the amide obtained in Step A and 4.62 g (30 mmol) of phosphorus oxychloride are dissolved in 40 ml of anhydrous pyridine. The reaction medium is then heated at reflux for 1 hour under an inert atmosphere; the solvent is then evaporated in vacuo. The residue obtained is slowly hydrolysed with a saturated solution of sodium hydrogen carbonate; the aqueous phase is then extracted with dichloromethane. The organic phase, dried over magnesium sulphate and then filtered, is concentrated in vacuo. The title nitrile is obtained pure in the form of a white solid after passage over a silica column (eluant:AcOEt/PE:10/60).

Melting point: 92° 0 C.

Step C: (7-Methoxy-1,4-benzodioxin-2-yl)methanamine

The same procedure is used as in Step B of Example 17, starting from the compound obtained in Step B.

Step D: N-[(7-Methoxy-1,4-benzodioxin-2-yl)methyl]acetamide

The crude amine obtained in Step C is dissolved in 10 ml of anhydrous pyridine; the mixture is then cooled to 0° C. 0.41 g (4 mmol) of acetic anhydride is added to that solution; stirring is then maintained for 30 minutes. The solvent is then evaporated in vacuo; the residue is then taken up in dichloromethane. The organic phase is then acidified with a hydrochloric acid solution (1N); the aqueous phase is then extracted with dichloromethane. After drying over magnesium sulphate and evaporation of the solvent in vacuo, the title amide is obtained pure in the form of a white solid after passage over a silica column (eluant:MeOH/$CH_2Cl_2$: 10/90).

Melting point: 106° C.

EXAMPLE 25

N-[(7-Methoxy-1,4-benzodioxin-2-yl)methyl]-1-cyclopropanecarboxaimide

The amine obtained in Step C of Example 24 is dissolved in 16 ml of anhydrous dichloromethane and the mixture is cooled to 0° C. 2.5 ml (18 mmol) of triethylamine and 0.467 g (4.48 mmol) of cyclopropanecarboxylic acid chloride are slowly added to the medium. After 25 minutes of stirring under an argon atmosphere, the solution is acidified with a hydrochloric acid solution (1N); the aqueous phase is then extracted with dichloromethane. The organic phase, dried over magnesium sulphate and then filtered, is concentrated in vacuo. The title amide is obtained pure after passage over a silica column (eluant:MeOH/$CH_2Cl_2$: 2/98) in the form of a white solid.

Melting point: 137° C.

EXAMPLE 26

N-[(7-Methoxy-1,4-benzodioxin-2-yl)methyl]-N'-propylurea

The amine obtained in Step C of Example 24 is dissolved in 16 ml of anhydrous toluene; 0.78 g (9.17 mmol) of n-propyl isocyanate is then added to the medium. After 4 hours of stirring under an inert atmosphere and at ambient temperature, the excess of isocyanate is neutralised with a few drops of water. The solvent is then evaporated in vacuo. The residue obtained is purified on a silica column (eluant:MeOH/CH$_2$Cl$_2$: 10/90) to yield the title urea in the form of a white solid.

Melting point: 141–142° C.

EXAMPLE 27

N-[2-(1,4-Benzodioxin-2-yl)ethyl]acetamide

The amine obtained in Preparation 7 is taken up in 5 ml of anhydrous pyridine; the temperature is then lowered to 0° C. 0.484 g (4.74 mmol) of acetic anhydride is then added to the medium. After 30 minutes of stirring under an inert atmosphere, the solvent is evaporated in vacuo; the residue is then taken up in dichloromethane. The organic phase is acidified with a hydrochloric acid solution (1N); the aqueous phase is then extracted with dichloromethane. The organic phase, dried over magnesium sulphate and then filtered, is concentrated in vacuo. The title amide is obtained pure in the form of a chestnut-brown syrup after passage over a silica column (eluant:AcOEt/PE:80/20).

EXAMPLE 28

N-[2-(1,4-Benzodioxin-2-yl)ethyl]-1-cyclopropanecarboxaimide

The amine obtained in Preparation 7 is taken up in 10 ml of anhydrous dichloromethane; the mixture is then cooled to 0° C. 0.383 g (3.66 mmol) of cyclopropanecarboxylic acid chloride and 0.74 g (7.32 mmol) of triethylamine are then added to the medium. After 30 minutes of stirring at 0° C. and under an inert atmosphere, the reaction mixture is acidified with a hydrochloric acid solution (1N); the aqueous phase is then extracted with dichloromethane. The organic phase, dried over magnesium sulphate and then filtered, is concentrated in vacuo. The title amide is obtained pure in the form of a white solid after passage over a silica column (eluant:AcOEt/PE:70/30).

| Melting point: 109° C. Elemental microanalysis: | | | |
|---|---|---|---|
| | C | H | N |
| % Calculated | 68.56 | 6.16 | 5.71 |
| % Found | 68.41 | 6.21 | 5.51 |

EXAMPLE 29

N-[2-(1,4-Benzodioxin-2-yl)ethyl]-N'-propylurea

The amine obtained in Preparation 7 is taken up in 25 ml of anhydrous toluene; 0.3 g (3.55 mmol) of n-propyl isocyanate is then added to that solution. After 2 hours of stirring under argon and at ambient temperature, the excess of isocyanate is neutralised with water; the solvent is then evaporated in vacuo. The title urea is obtained pure in the form of a white solid after passage over a silica column (eluant:AcOEt/PE:70/30).

| Melting point: 121–122° C. Elemental microanalysis: | | | |
|---|---|---|---|
| | C | H | N |
| % Calculated | 64.11 | 6.92 | 10.68 |
| % Found | 65.00 | 6.99 | 10.24 |

EXAMPLE 30

N-[2-(1,4-Benzodioxin-2-yl)ethyl]-N'-propylthiourea

The title compound is obtained by treatment of the compound obtained in Example 29 with Lawesson's reagent.

EXAMPLE 31

N-[2-(1,4-Benzodioxin-2-yl)ethyl]-N-butylacetamide

The title compound is obtained by alkylation of the compound obtained in Example 27 with butyl iodide in a basic medium in DMF.

EXAMPLE 32

N-[(3-Phenyl-1,4-benzodioxin-2-yl)methyl]acetamide

Step A: 3-Phenyl-1,4-benzodioxin-2-carboxamide 2.96 g (11 mmol) of the ester obtained in Preparation 9 are dissolved in 70 ml of ethanol; 70 ml of a 28% solution of ammonia are then added to the medium. After 6 days of stirring at ambient temperature, the solvent is evaporated in vacuo. The residue obtained is purified on a silica column (eluant:MeOH/CH$_2$Cl$_2$: 5/95) to yield the title amide.

Melting point: 135° C.

Step B: 3-Phenyl-1,4-benzodioxin-2-carbonitrile 3.59 ml (30 mmol) of phosphorus oxychloride are slowly added to a solution of 1.52 g (6 mmol) of the amide obtained in Step A in 15 ml of anhydrous pyridine. The medium is then heated at reflux for 2 hours under argon and then allowed to cool. After evaporation of the solvent in vacuo, the residue obtained is diluted with dichloromethane; the organic phase is then hydrolysed with a saturated solution of sodium hydrogen carbonate. The aqueous phase is extracted with dichloromethane; the organic phase is then dried over magnesium sulphate. The solvent is then evaporated under reduced pressure. Chromatography on a silica column (eluant:AcOEt/PE:40/60) allows the title nitrile to be obtained in the form of a white solid.

Melting point: 85–86° C.

Step C: (3-Phenyl-1,4-benzodioxin-2-yl)methanamine

The same procedure is used as in Step C of Example 1, starting from the compound obtained in Step B. Yellow oil.

Step D: N-[(3-Phenyl-1,4-benzodioxin-2-yl)methyl]acetamide 0.416 ml (4.4 mmol) of acetic anhydride are slowly added to a solution of 0.88 g (3.67 mmol) of the amine obtained in Step C in 10 ml of anhydrous pyridine previously cooled to 0° C. After 1 hour of stirring under argon, the medium is diluted with dichloromethane and then acidified with a hydrochloric acid solution (1N). The aqueous phase is then extracted with dichloromethane; the organic phases are then dried over magnesium sulphate. The solvent is evaporated in vacuo; the residue obtained is then passed over a silica column (eluant:AcOEt/PE:60/40) to yield the title amide in the form of a white solid.

| | Melting point: 182° C. Elemental microanalysis: | | |
|---|---|---|---|
| | C | H | N |
| % Calculated | 72.58 | 5.37 | 4.98 |
| % Found | 72.38 | 5.57 | 5.18 |

EXAMPLE 33

N-[(3-Methyl-1,4-benzodioxin-2-yl)methyl] acetamide

The title compound is obtained after lithiation of the ester obtained in Preparation S using lithium diisopropylamide (LDA) and condensation of methyl iodide. The procedure is then as in Steps A, B, C and D of Example 32.

EXAMPLE 34

N-[(7-Methoxy-3-phenyl-1,4-benzodioxin-2-yl) methyl]acetamide

Step A: 7-Methoxy-3-phenyl-1,4-benzodioxin-2-carboxamide 120 ml of a 28% aqueous solution of ammonia are added to a solution of 0.94 g (3.15 mmol) of the ester obtained in Preparation 10 in 35 ml of ethanol. After 4 days of stirring at ambient temperature, the solvent is evaporated in vacuo. Chromatography on a silica column (eluant:methanol/dichloromethane:5/95) yields the title amide in the form of a white solid.

Melting point: 193° C.

Step B: 7-Methoxy-3-phenyl-1,4-benzodioxin-2-carbonitrile 0.9 ml (7.5 mmol) of phosphorus oxychloride are slowly added to a solution of 0.24 g (1.5 mmol) of the amide obtained in Step A in 5 ml of anhydrous pyridine. The reaction medium is heated at reflux for 1 hour under an inert atmosphere and then allowed to cool. After evaporation of the solvent in vacuo, the residue is taken up in dichloromethane and then hydrolysed with a saturated solution of sodium hydrogen carbonate. The aqueous phase is then extracted with dichloromethane. The organic phase, dried over magnesium sulphate and then filtered, is concentrated in vacuo. The residue obtained is passed over a silica column (eluant:AcOEt/PE:25/75) to yield the title nitrile in the form of a white solid.

Melting point: 94–95° C.

Step C: (7-Methoxy-3-phenyl-1,4-benzodioxin-2-yl)methanamine

The same procedure is used as in Step C of Example 1, starting from the compound obtained in Step B. Yellow oil.

Step D: N-[(7-Methoxy-3-phenyl-1,4-benzodioxin-2-yl)methyl]acetamide 0.2 g (0.74 mmol) of the amine obtained in Step C is dissolved in 3 ml of anhydrous pyridine; the solution is then cooled to 0° C. After addition of 0.085 ml (0.89 mmol) of acetic anhydride, the reaction medium is stirred for 1 hour at 0° C. The solution is then diluted with dichloromethane and then acidified with a hydrochloric acid solution (1N). The aqueous phase is extracted with dichloromethane; the organic phase is then dried over magnesium sulphate. After evaporation of the solvent in vacuo, the residue obtained is purified on a silica column (eluant:AcOEt/PE:60/40) to yield the title amide in the form of a white solid.

| | Melting point: 173° C. Elemental microanalysis: | | |
|---|---|---|---|
| | C | H | N |
| % Calculated | 69.44 | 5.50 | 4.50 |
| % Found | 68.94 | 5.77 | 4.66 |

EXAMPLE 35

N-[(3-Benzyl-7-methoxy-1,4-benzodioxin-2-yl) methyl]acetamide

The title compound is obtained after lithiation using LDA of the ester obtained in Preparation 8 and condensation with benzyl iodide. The procedure is then as in Steps A, B, C and D of Example 32.

EXAMPLE 36

N-[(6-Methoxy-3,4-dihydro-2H-3-chromenyl) methyl]acetamide 0.935 g (5 mmol) of the nitrile obtained in Preparation 11 and 0.623 g (7.5 mmol) of sodium acetate are added to a suspension of 0.44 g of Raney nickel in 20 ml of acetic anhydride; the mixture is then subjected to hydrogen pressure of 50 psi at a temperature of 50° C. for 24 hours. After cooling, the salts are filtered off; the solvent is then evaporated in vacuo. The residue obtained is taken up in ethyl acetate; the organic phase is then washed with a saturated solution of sodium hydrogen carbonate. After drying over magnesium sulphate and filtration, the filtrate is concentrated in vacuo. Chromatography on a silica column (eluant:AcOEt) yields the title amide in the form of a white solid.

| | Melting point: 110° C. Elemental microanalysis: | | |
|---|---|---|---|
| | C | H | N |
| % Calculated | 66.36 | 7.28 | 5.95 |
| % Found | 66.54 | 7.40 | 5.90 |

EXAMPLE 37

N-[(6-Methoxy-3,4-dihydro-2H-3-chromenyl) methyl]-1-cyclobutanecarboxamide

The procedure is as in Step C of Example 1, starting from the compound obtained in Preparation 11; cyclobutanecarboxylic anhydride is then condensed to yield the title compound.

EXAMPLE 38

N-[2-(6-Methoxy-3,4-dihydro-2H-3-chromenyl) ethyl]acetamide

Step A: (6-Methoxy-3,4-dihydro-2H-3-chromenyl)methanol 2 g (10.5 mmol) of the alcohol obtained in Preparation 12 are dissolved in 60 ml of ethanol; 0.616 g (10.5 mmol) of Raney nickel previously washed in ethanol is then added to that solution. The reaction medium is subjected to hydrogen pressure of 50 psi for 22 hours. The remaining catalyst is filtered off; the solvent is then evaporated in vacuo. Chromatography on a silica column (eluant:AcOEt/PE:50/50) results in the pure title alcohol in the form of a white solid.

Melting point: 56–57° C.

Step B: [(6-Methoxy-3,4-dihydro-2H-3-chromenyl)methyl] 4-methyl-1-benzeneulphonate 1.83 g (9.44 mmol) of the alcohol obtained in Step A are dissolved in 40 ml of anhydrous dichloromethane; 3.15 g (16.5 mmol) of para-toluenesulphonyl chloride and 4.6 ml (33 mmol) of triethylamine are then added in succession to the medium. After 21 hours of stirring at ambient temperature and under argon, the solvent is evaporated under reduced pressure. The title tosylate is obtained pure in the form of a clear oil after passage over a silica column (eluant:AcOEt/PE:15/85 then 30/70).

Step C: 2-(6-Methoxy-3,4-dihydro-2H-3-chromenyl) acetonitrile 1.6 g (4.56 mmol) of the tosylate obtained in Step B are dissolved in 25 ml of anhydrous N,N-dimethylformamide; 0.724 g (11.5 mmol) of potassium cyanide is then added to the solution. After 4 hours of reflux under argon, the solvent is evaporated in vacuo; the residue is then taken up in a saturated solution of sodium hydrogen carbonate. The aqueous phase is then extracted with dichloromethane. The organic phases, dried over magnesium sulphate and then filtered, are concentrated under reduced pressure. The title nitrile is obtained pure in the form of an oil which crystallises slowly after chromatography on silica gel (eluant:AcOEt/PE:25/75).

Melting point: 54–55° C.

Step D: N-[2-(6-Methoxy-3,4-dihydro-2H-3-chromenyl) ethyl]acetamide 0.812 g (4 mmol) of the nitrile obtained in Step C is added to a suspension of 0.35 g (6 mmol) of Raney nickel and 0.5 g (6 mmol) of sodium acetate in 40 ml of acetic anhydride. The reaction medium is then subjected to hydrogen pressure of 50 psi at a temperature of 50° C. for 5 hours. After cooling of the mixture, the salts are filtered off and the filtrate is concentrated under reduced pressure. The residue obtained is then taken up in ethyl acetate; the organic phase is then washed with a saturated solution of sodium hydrogen carbonate. After drying over magnesium sulphate and filtration, the solvent is evaporated in vacuo. Chromatography on a silica column (eluant:AcOEt) results in the title amide in the form of a white solid.

Melting point: 114° C.
Elemental microanalysis:

|  | C | H | N |
|---|---|---|---|
| % Calculated | 67.45 | 7.68 | 5.62 |
| % Found | 67.72 | 7.71 | 5.62 |

EXAMPLE 39

N-Methyl-N-phenyl-2-(6-methoxy-3,4-dihydro-2H-3-chromenyl)acetamide

The title compound is obtained after hydrolysis of the nitrile obtained in Step C of Example 38, conversion into the corresponding acid chloride and condensation with N-methyl-N-phenylamine.

EXAMPLE 40

N-[(6-Methoxy-2H-3-chromenyl)methyl]acetamide

Step A: 3-(Bromomethyl)-6-methoxy-2H-chromene 1.34 g (7 mrnol) of the alcohol obtained in Preparation 12 are dissolved in 15 ml of acetonitrile; 2.95 g (7 mmol) of dibromotriphenylphosphorane are then added to that solution. After 15 minutes of stirring at ambient temperature and under an inert atmosphere, the solvent is evaporated in vacuo. The residue obtained is then taken up in 50 ml of an ether/hexane mixture 1:1; the medium is then stirred for one hour. The salts are filtered off and then washed several times with the ether/hexane mixture 1:1. The organic phases are concentrated in vacuo to yield the brominated compound of the title in the form of a brown solid.

Step B: (6-Methoxy-2H-3-chromenyl)methanamine 1.17 g (4.59 mmol) of the brominated compound obtained in Step A are dissolved in 10 ml of anhydrous N,N-dimethylformamide; 1.275 g (6.9 mmol) of potassium phthalimide are then added to the medium. After 10 hours of stirring under argon, the solvent is evaporated in vacuo. The residue obtained is taken up in dichloromethane; the organic phase is then washed with water. After drying over magnesium sulphate, the solvent is evaporated in vacuo. Chromatography on a silica column (eluant:AcOEt/PE:15/85) allows access to the corresponding phthalimide in the form of a white solid. Melting point: 141° C. 0.72 g (14.35 mmol) of hydrazine monohydrate is added to a solution of 1.15 g (3.58 mmol) of that phthalimide in 20 ml of THF; the mixture is then heated at reflux for 4 hours. After cooling the mixture and filtering off the solid, the filtrate is concentrated in vacuo to result in the pure title amine in the form of a yellow solid.

Step C: N-[(6-Methoxy-2H-3-chromenyl)methyl]acetamide

The procedure is as in Step D of Example 1, starting from the amine obtained in Step B.

Melting point: 128° C.
Elemental microanalysis:

|  | C | H | N |
|---|---|---|---|
| % Calculated | 66.94 | 6.48 | 6.00 |
| % Found | 66.41 | 6.65 | 5.95 |

EXAMPLE 41

N-[(6-Methoxy-2H-3-chromenyl)methyl]butanamide

A solution of 0.49 g (2.57 mmol) of the amine obtained in Step B of Example 40 in 10 ml of dichloromethane is cooled to 0° C.; 1 ml (7.7 mmol) of triethylamine and also 0.41 g (3.85 mmol) of butyryl chloride are then added in succession to the medium. After 30 minutes of stirring under an inert atmosphere, the reaction mixture is acidified with a hydrochloric acid solution (1N); the aqueous phase is then extracted with dichloromethane. The organic phase, dried over magnesium sulphate and then filtered, is concentrated in vacuo. Chromatography on a silica column (eluant:PE/AcOEt:40/60) yields the title amide in the form of a white solid.

| | C | H | N |
|---|---|---|---|
| | Melting point: 90° C. Elemental microanalysis: | | |
| % Calculated | 68.94 | 7.33 | 5.36 |
| % Found | 68.85 | 7.35 | 5.33 |

EXAMPLE 42

N-[(6-Methoxy-2-phenyl-2H-3-chromenyl)methyl]acetamide

Step A: (6-Methoxy-2-phenyl-2H-3-chromenyl)methanol 3.8 g (25 mmol) of 2-hydroxy-5-methoxybenzaldehyde are added to a solution of 3.63 g (27.5 mmol) of cinnamaldehyde in 25 ml of N,N-dimethylformamide; 3.8 g (27.5 mmol) of potassium carbonate are then added to the medium. After 10 minutes of reflux, the reaction mixture is concentrated in vacuo; the residue is then taken up in water. The aqueous phase is extracted with ethyl acetate; the organic phase is then dried over magnesium sulphate. After evaporation of the solvent in vacuo, the crude product is dissolved in 30 ml of anhydrous ethanol; 0.95 g (25 mmol) of sodium borohydride is then added to the medium. The solution is stirred under argon for 15 minutes; the solvent is then evaporated in vacuo. The residue obtained is dissolved in water and then hydrolysed with a 1N hydrochloric acid solution. The aqueous phase is extracted with ethyl acetate; the organic phase is then dried over magnesium sulphate. After evaporation of the solvent in vacuo, chromatography on a silica column (eluant:AcOEt/PE:30/70 then 40/60) yields the title alcohol in the form of a yellow solid in a yield of 47%.

Melting point: 120° C.

Step B: 3-(Bromomethyl)-2-phenyl-6-methoxy-2H-chromene 4.79 g (8.95 mmol) of dibromotriphenylphosphorane are added to a solution of 2.4 g (8.95 mmol) of the alcohol obtained in Step A in 80 ml of acetonitrile. After 15 minutes of stirring under argon, the solvent is evaporated in vacuo; the residue obtained is then taken up in an ether/hexane mixture (1/1). The solid formed is filtered off; the filtrate is then concentrated under reduced pressure to yield the brominated compound of the title in the form of a chestnut-brown syrup.

Step C: (6-Methoxy-2-phenyl-2H-3-chromenyl)methanamine 2.36 g (12.76 mmol) of potassium phthalimide are added to a solution of 2.82 g (8.5 mmol) of the brominated compound obtained in Step B; the medium is then stirred for 10 hours. The solvent is evaporated in vacuo; the residue obtained is then taken up in water. The aqueous phase is extracted with dichloromethane. The organic phase, dried over magnesium sulphate, is concentrated in vacuo. The crude product is purified on a silica column (eluant:AcOEt/CH$_2$Cl$_2$/PE:15/15/70) to yield the corresponding phthalimide in the form of a white solid (melting point: 150° C.) which is redissolved, together with 0.74 ml (15.12 mmol) of hydrazine monohydrate, in 20 ml of THF and heated at reflux for 4 hours. The mixture is allowed to cool; the solid formed is then filtered off. Evaporation of the filtrate in vacuo yields the title amine in the form of a yellow solid in a yield of 98%.

Melting point: 97–98° C.

Step D: N-[(6-Methoxy-2-phenyl-2H-3-chromenyl)methyl]acetamide

A solution of 0.42 g (1.57 mmol) of the amine obtained in Step C in 5 ml of anhydrous pyridine is cooled to 0° C.; 0.18 ml (1.97 mmol) of acetic anhydride is then added to the medium. After 30 minutes of stirring under argon, the medium is diluted with dichloromethane and then adjusted to an acid pH with 1N hydrochloric acid solution. The aqueous phase is extracted with dichloromethane; the organic phase is then washed with a saturated solution of sodium hydrogen carbonate. The residue obtained, after evaporation of the solvent in vacuo, is purified on a silica column (eluant:AcOEt/PE:70/30) to yield the title amide in the form of a white solid.

| | C | H | N |
|---|---|---|---|
| | Melting point: 147–148° C. Elemental microanalysis: | | |
| % Calculated | 73.77 | 6.19 | 4.53 |
| % Found | 73.17 | 6.46 | 4.49 |

EXAMPLE 43

N-[(6-Methoxy-2-phenyl-2H-3-chromenyl)methyl]butanamide

A solution of 0.45 g (1.7 mmol) of the amine obtained in Step C of Example 42 in 15 ml of anhydrous dichloromethane is cooled to 0° C.; 0.7 ml (5.1 mmol) of triethylamine and also 0.26 ml (2.55 mmol) of butynyl chloride are then added to the medium. Stirring is maintained for 30 minutes; the reaction mixture is then adjusted to an acid pH with a 1N hydrochloric acid solution. The aqueous phase is extracted with dichloromethane; the organic phase is then washed with a saturated solution of sodium hydrogen carbonate. The residue obtained after evaporation of the solvent in vacuo is passed over a silica column (eluant:AcOEt/PE:60/40) to yield the title amide in the form of a white solid.

| | C | H | N |
|---|---|---|---|
| | Melting point: 136–137° C. Elemental microanalysis: | | |
| % Calculated | 74.75 | 6.87 | 4.15 |
| % Found | 74.68 | 7.12 | 4.17 |

EXAMPLE 44

N-(2,3-Dihydro-8H-[1,4]-dioxino[2,3-f]chromen-9-yl-methyl)acetamide

A solution of 0.37 g (1.69 mmol) of the amine obtained in Preparation 13 in 3 ml of anhydrous pyridine is cooled to 0° C.; 0.21 g (0.19 ml, 2 mmol) of acetic anhydride is then added to the medium. After 30 minutes of stirring at 0° C. and under argon, the mixture is diluted with dichloromethane and then adjusted to an acid pH with a 1N hydrochloric acid solution. The aqueous phase is then extracted with dichloromethane. The organic phase, dried over magnesium sulphate and then filtered, is concentrated in vacuo. Chromatography on a silica column (eluant:ethyl acetate/petroleum ether:80/20) yields the title amide in the form of a white solid.

| | Melting point: 151–153° C. Elemental microanalysis: | | |
|---|---|---|---|
| | C | H | N |
| % Calculated | 64.35 | 5.79 | 5.36 |
| % Found | 64.10 | 5.92 | 5.32 |

EXAMPLE 45

N-(2,3-Dihydro-8H-[1,4]-dioxino[2,3-f]chromen-9-yl-methyl)butanamide

A solution of 0.4 g (1.83 mmol) of the amine obtained in Preparation 13 in 15 ml of anhydrous dichloromethane is cooled to 0° C.; 0.29 g (0.3 ml, 2.74 mmol) of butanoyl chloride is added to the medium. After 30 minutes of stirring under argon, the medium is acidified with a 1N hydrochloric acid solution; the aqueous phase is then extracted with dichloromethane. The organic phase, dried over magnesium sulphate and then filtered, is concentrated in vacuo. Chromatography on a silica column (eluant:ethyl acetate/petroleum ether:50/50) yields the title amide in the form of a white solid.

| | Melting point: 110–112° C. Elemental microanalysis: | | |
|---|---|---|---|
| | C | H | N |
| % Calculated | 66.42 | 6.62 | 4.84 |
| % Found | 66.32 | 6.67 | 4.96 |

EXAMPLE 46

N-[(6-Methoxy-3,4-dihydro-2H-4-chromenyl)methyl]acetamide

Step A: 6-Methoxy-4-chromancarbonitrile

In an anhydrous medium, the compound obtained in Step C of Example 12 (500 mg; 2.8 mmol) and diethyl cyanophosphonate (2 eq; 8.4 mmol; 16.8 ml) are mixed in 25 ml of THF. After 30 minutes of stirring, the reaction mixture is hydrolysed and then extracted with AcOEt. In parallel, a solution of samarium iodide is prepared. The samarium (4.5 eq; 12.6 mmol; 1.9 g) is suspended in 15 ml of THF; diiodoethane (3 eq; 8.4 mmol; 2.37 g), diluted in 15 ml of THF, is then added dropwise. When the samarium iodide solution has become blue, the complex previously formed is dissolved in 5 ml of THF and 0.3 ml of tert-butanol and then added to that solution of SmI2. The solution is stirred for 12 hours at ambient temperature.

The reaction mixture is hydrolysed with a 10% HCl solution. After extraction with AcOEt, the organic phase is washed with a 10% solution of $Na_2S_2O_3$ and then twice with a saturated solution of $NaHCO_3$.

The residue obtained is purified by flash chromatography on silica gel (eluant:PE/AcOEt (8/2)). The title product is obtained in the form of an oil.

Step B: N-[(6-Methoxy-3,4-dihydro-2H-4-chromenyl)methyl]acetamide

The nitrile obtained in Step A (200 mg; 1.05 mmol) is solubilised in the reactor of a Parr apparatus in 15 ml of acetic anhydride. Raney nickel (60 mg; 30% by weight) and also sodium acetate (1.5 eq; 1.58 mmol; 130 mg) are added. The reactor is placed under hydrogen pressure of 580 psi at 50° C. for 12 hours. When the reaction is complete, filtration over Celite and then rinsing with AcOEt are carried out. The product is purified by flash chromatography on silica gel (eluant:AcOEt (100%)). The white solid obtained is recrystallised from a pentane-ether mixture.

| | Melting point: 140–141° C. Elemental microanalysis: | | |
|---|---|---|---|
| | C | H | N |
| % Calculated | 66.36 | 7.28 | 5.95 |
| % Found | 66.43 | 7.40 | 5.95 |

EXAMPLE 47

N-[(6-Methoxy-3,4-dihydro-2H-4-chromenyl)methyl]butanamide

In an anhydrous medium, at 0° C., the nitrile obtained in Step A of Example 46 (500 mg; 2.64 mmol) is solubilised in 5 ml of ether; $LiAlH_4$ (126 mg; 5.5 mmol; 2.1 eq) is then added in portions. The mixture is heated at reflux for 2 hours. Hydrolysis of the reaction mixture is carried out using 130 μl of water, 130 μl of a 15% solution of NaOH, and then with 370 μl of water. The salts are filtered off on a frit and rinsed with $CH_2Cl_2$; the solvents are then removed under reduced pressure. The amine thus obtained (300 mg; 1.53 mmol.) is dissolved in 6 ml of $CH_2Cl_2$, at 0° C. Triethylamine (3 eq; 4.59 mmol; 640 μl) and butyryl chloride (1.4 eq; 2.14 mmol; 222 μl) are added. Stirring is carried out, at ambient temperature, for 5 hours. After evaporation of the solvent, the product is extracted with $CH_2Cl_2$. The residue is purified by flash chromatography on silica gel (eluant AcOEt/PE (1/1)). The title product is obtained in the form of an oil.

| | Elemental microanalysis: | | |
|---|---|---|---|
| | C | H | N |
| % Calculated | 68.41 | 8.04 | 5.32 |
| % Found | 68.42 | 8.23 | 5.15 |

EXAMPLE 48

N-[2-(6-Methoxy-3,4-dihydro-2H-4-chromenyl)ethyl]-3-butanamide

In an anhydrous medium, the nitrile obtained in Step E of Example 12 (740 mg; 3.64 mmol) is solubilised in 30 ml of ether; $LiAlH_4$ (1.5 eq; 5.46 mmol; 207 mg) is then added in portions. The mixture is heated at reflux for 3 hours, under argon. After returning to ambient temperature, 210 μl of water, 210 μl of a 15% solution of NaOH, and then 620 μl of water are added in succession. The solution is stirred for 30 minutes at ambient temperature. The salts are filtered off on a frit; the filtrate is dried over $MgSO_4$ and evaporated under reduced pressure. The yellow oil obtained is used immediately in the following Step:in an anhydrous medium, at −10° C., 3-butanoic acid (1.5 eq; 5.43 mmol; 467 mg) and HOBT (1.5 eq; 5.43 mmol; 733 mg). The mixture is stirred, under argon, at −10° C. for 30 minutes. In parallel, the amine is dissolved in 10 ml of distilled $CH_2Cl_2$ and placed in the presence of triethylamine (1 eq; 3.62 mmol; 504 µl). The "activated" 3-butanoic acid is then added to the solution of free amine. The reaction medium is left for 2 hours at −10° C., and then for 60 hours at ambient temperature. The mixture is then washed in succession with 1N HCl, with water, with 1N NaOH and with water and dried over $MgSO_4$; the solvent is evaporated under reduced pressure. The residue obtained is purified by flash chromatography on silica gel (eluant:PE/AcOEt (3/7)). The product is obtained in the form of white crystals after washing with ether.

Melting point: 73–74° C.
Elemental microanalysis:

|  | C | H | N |
|---|---|---|---|
| % Calculated | 69.79 | 7.69 | 5.09 |
| % Found | 69.57 | 7.67 | 5.17 |

EXAMPLE 49

N-[2-(2,3-Dihydro-1,4-benzodioxin-2-yl)ethyl] acetamide

Step A: 2-(2,3-Dihydro-1,4-benzodioxin-2-yl)ethyl 4-methyl-1-benzenesulphonate 2.86 g (15 mmol) of tosyl chloride are added to a solution of 1.66 g (10 mmol) of the alcohol in Step A of Example 20 and also 3 g (30 mmol) of triethylamine in 50 ml of dichloromethane. After 20 hours of stirring at ambient temperature and under argon, the solvent is evaporated in vacuo. The residue thus obtained is passed over a silica column (eluant:ethyl acetate/petroleum ether 7/93) to yield the title tosylate in the form of a white solid.

Melting point: 68° C.

Step B: 2-(Iodomethyl)-2,3-dihydro-1,4-benzodioxin

A solution of 1.2 g (3.75 mmol) of the tosylate obtained in Step A and 1.12 g (7.5 mmol) of sodium iodide in 20 ml of acetone is heated at reflux, under argon, for 36 hours. After evaporation of the solvent in vacuo, the residue obtained is taken up in water and then extracted with dichloromethane. The organic phase is dried over magnesium sulphate and then concentrated in vacuo. Chromatography on a silica column (eluant:petroleum ether/ethyl acetate:90/10) allows the iodinated compound of the title to be obtained in the form of a white solid in a yield of 90%.

Melting point: 38–40° C.

Step C: 2-(2,3-Dihydro-1,4-benzodioxin-2-yl)acetonitrile

The procedure is as in Step D of Example 22.

Step D: N-[2-(2,3-Dihydro-1,4-benzodioxin-2-yl)ethyl] acetamide 0.405 g (2.31 mmol) of the nitrile obtained in Step C is added to a solution of 0.2 g (3.47 mmol) of Raney nickel and also 0.28 g (3.47 mmol) of sodium acetate in 10 ml of acetic anhydride; the whole is then heated at 50° C. under hydrogen pressure of 50 psi for 6 hours. After filtering off the remaining catalyst, the solvent is evaporated in vacuo; the residue thus obtained is then washed with a saturated solution of sodium hydrogen carbonate. The aqueous phase is extracted with ethyl acetate; the organic phase is then dried over magnesium sulphate. After evaporation of the solvent in vacuo, chromatography on a silica column (eluant:dichloromethane/methanol 96/4) yields the title amide in the form of a clear oil.

EXAMPLE 50

N-[(6-Methoxy-3,4-dihydro-2H-3-chromenyl) methyl]butanamide

Step A: 6-Methoxy-3-chromancarbonitrile 0.9 g (4.8 mmol) of the nitrile obtained in Preparation 11 is added to a suspension of 0.09 g of palladium/carbon in 15 ml of anhydrous methanol; the mixture is then subjected to hydrogen pressure of 50 psi for 22 hours. After filtering off the remaining catalyst, the solvent is evaporated in vacuo; the crude reaction product is then purified on a silica column (eluant:petroleum ether/ethyl acetate 75/25) to yield the title nitrile in the form of a white solid.

Melting point: 79–80° C.

Step B: (6-Methoxy-3,4-dihydro-2H-3-chromenyl) methylamine 0.51 g (2.7 mmol) of the nitrile obtained in Step A is reduced with lithium aluminium hydride in ether to yield the title amine in the form of a yellow oil.

Step C: N-[(6-Methoxy-3,4-dihydro-2H-3-chromenyl) methyl]butanamide

A solution of 0.4 g (2.06 mmol) of the amine obtained in Step B in 20 ml of anhydrous dichloromethane is cooled to 0° C. 1 ml (7.2 mmol) of triethylamine and also 0.38 g (3.6 mmol) of butyryl chloride are added in succession to the medium. After one hour of stirring s under argon, the reaction mixture is acidified with a 1N hydrochloric acid solution; the aqueous phase is then extracted with dichloromethane. The organic phase is dried over magnesium sulphate and then concentrated in vacuo. The title amide is obtained pure in the form of a white solid after passage over a silica column (eluant:petroleum ether/ethyl acetate 50/50).

Melting point: 110–111° C.
Elemental microanalysis:

|  | C | H | N |
|---|---|---|---|
| % Calculated | 68.41 | 8.04 | 5.32 |
| % Found | 68.59 | 8.13 | 5.39 |

EXAMPLE 51

N-[2-(9-Methoxy-2,3-dihydro-1H-benzo[f]chromen-1-yl)ethyl]acetamide

The nitrile obtained in Preparation 16 (400 mg; 1.58 mmol) is solubilised in a Parr reactor in 22 ml of acetic anhydride. Raney nickel (60 mg; 30% by weight) and also sodium acetate (1.5 eq; 2.37 mmol; 208 mg) are added. The reactor is placed under hydrogen pressure of 50 psi. After 12 hours of reaction at 50° C., the reaction mixture is filtered over Celite and then rinsed with $CH_2Cl_2$. The different solvents are evaporated; the residue is then hydrolysed and extracted with AcOEt. The product is purified by flash chromatography on silica gel (eluant:AcOEt (100%) then AcOEt/MeOH (95/5)). The solid is obtained after recrystallisation from ether containing a few drops of isopropanol.

Melting point: 106–107° C.
Elemental microanalysis:

|  | C | H | N |
|---|---|---|---|
| % Calculated | 72.21 | 7.07 | 4.68 |
| % Found | 71.81 | 7.22 | 4.70 |

EXAMPLE 52

N-[2-(9-Methoxy-2,3-dihydro-1H-benzo[f]chromen-1-yl)ethyl]butanamide

In an anhydrous medium and at 0° C., the nitrile obtained in Preparation 16 (200 mg; 0.79 mmol) is solubilised in 5 ml of ether; LiAlH$_4$ (2.1 eq; 1.66 mmol; 63 mg) is then added in portions. The mixture is heated at reflux for 2 hours. Hydrolysis of the medium is carried out with 64 μl of water, 64 μl of a 15% solution of NaOH and then 190 μl of water. The salts are filtered off on a frit and rinsed with ether; the solvents are then removed under reduced pressure. The amine thus obtained (0.79 mmol) is dissolved in 2 ml of CH$_2$Cl$_2$, at 0° C. Triethylamine (3 eq; 1.87 mmol; 260 μl) and also butyryl chloride (1.4 eq; 1.11 mmol; 115 μl) are added. Stirring is carried out at ambient temperature for 2 hours. After evaporation of the solvent, the product is extracted with CH$_2$Cl$_2$. The residue is purified by flash chromatography on silica gel (eluant:CH$_2$Cl$_2$ (100%) then CH$_2$Cl$_2$/MeOH (95/5)). The title product is obtained in the form of a solid after recrystallisation from the mixture Et$_2$O/EtOH (8/2).

| Melting point: 114° C. Elemental microanalysis: | | | |
|---|---|---|---|
| | C | H | N |
| % Calculated | 73.36 | 7.70 | 4.28 |
| % Found | 73.00 | 7.56 | 4.18 |

EXAMPLE 53

N-[2-(9-Methoxy-2,3-dihydro-1H-benzo[f]chromen-1-yl)methyl]acetamide

The nitrile obtained in Preparation 15 (200 mg; 0.84 mmol) is solubilised in a Parr reactor in 15 ml of acetic anhydride. Raney nickel (60 mg; 30% by weight) and also sodium acetate (3 eq; 2.52 mmol; 200 mg) are added. The reactor is placed under hydrogen pressure of 50 psi. After 12 hours of reaction at 50° C., the reaction mixture is filtered over Celite and then rinsed with CH$_2$Cl$_2$. The different solvents are evaporated; the residue is then hydrolysed and extracted with AcOEt. The product is purified by flash chromatography on silica gel (eluant:CH$_2$Cl$_2$/MeOH (95/5)). The title compound is obtained in the form of a solid after washing with ether.

| Melting point: 145–147° C. Elemental microanalysis: | | | |
|---|---|---|---|
| | C | H | N |
| % Calculated | 71.55 | 6.71 | 4.91 |
| % Found | 71.84 | 6.66 | 5.04 |

EXAMPLE 54

N-[2-(9-Methoxy-2,3-dihydro-1H-benzo[f]chromen-1-yl)methyl]butanamide

In an anhydrous medium and at 0° C., the nitrile obtained in Preparation 15 (300 mg; 1.25 mmol) is solubilised in 5 ml of ether; LiAlH$_4$ (3 eq; 3.75 mmol; 143 mg) is then added in portions. The mixture is heated at reflux for 3 hours. The mixture is hydrolysed with 220 μl of water, 64 μl of a 15% solution of NaOH, and then 650 μl of water. The salts are filtered off on a frit and rinsed with CH$_2$Cl$_2$; the solvents are then removed under reduced pressure. The amine thus obtained (300 mg; 1.53 mmol) is dissolved in 6 ml of CH$_2$Cl$_2$, at 0° C. Triethylamine (3 eq; 3.76 mmol; 254 μl) and also butyryl chloride (1.4 eq; 1.76 mmol; 183 μl) are added. Stirring is carried out at ambient temperature for 5 hours. After evaporation of the solvent, the product is extracted with CH$_2$Cl$_2$. The residue is purified by flash chromatography on silica gel (eluant:AcOEt/PE (7/3)). The title product is obtained in the form of a white solid after crystallisation from ether.

| Melting point: 118–119° C. Elemental microanalysis: | | | |
|---|---|---|---|
| | C | H | N |
| % Calculated | 72.81 | 7.40 | 4.47 |
| % Found | 72.49 | 7.40 | 4.71 |

EXAMPLE 55

N-{[(6-(Pentyloxy)-2H-3-chromenyl]methyl}acetamide

Step A: 6-Hydroxy-2H-3-chromenecarbaldehyde 3 g (21.7 mmol) of 2,5-dihydroxybenzaldehyde and also 2.2 ml (32.6 mmol) of acrolein are added to a suspension of 6 g (43.5 mmol) of potassium carbonate in 50 ml of 1,4-dioxane; the medium is then heated at reflux for 12 hours. The salts are filtered off over Celite; the solvent is then evaporated in vacuo. The residue obtained is taken up in water; the aqueous phase is then extracted with ether. After drying over magnesium sulphate and evaporation of the solvent in vacuo, the crude product is triturated in dichloromethane to yield the title compound in the form of a yellow solid.

Melting point: 165° C.

Step B: 6-(Pentyloxy)-2H-3-chromenecarbaldehyde 2 g (11.4 mmol) of the hydroxyaldehyde obtained in Step A and also 2.7 g (13.6 mmol) of iodopentane are added to a suspension of 1.9 g (13.6 mmol) of potassium carbonate in 50 ml of anhydrous acetone; the medium is then heated at reflux. After one hour, 1.2 g of potassium carbonate are added to the solution, and that operation is then re-started after one hour. At the end of 12 hours of heating at reflux, the solution is allowed to cool, the salts are filtered off over Celite and the solvent is then evaporated in vacuo. Chromatography on a silica column (eluant:petroleum ether/ethyl acetate 90/10) yields the title aldehyde in the form of a yellow syrup.

Step C: [6-(Pentyloxy)-2H-3-chromenyl]methanol 0.22 g (5.7 mmol) of sodium borohydride is added all at once to a suspension of 1.4 g (5.7 mmol) of the aldehyde obtained in Step B in 20 ml of anhydrous ethanol. After 15 minutes of stirring under argon, the solvent is evaporated in vacuo; the residue obtained is then acidified with a 1N hydrochloric acid solution. The aqueous phase is extracted with ethyl acetate; the organic phase is then dried over magnesium sulphate. The solvent is then evaporated under reduced pressure; the crude product is then purified on a silica column (eluant:ethyl acetate/petroleum ether 40/60) thus yielding the title alcohol in the form of a yellow syrup.

Step D: 3-(Bromomethyl)-2H-6-chromenyl pentyl ether 2 g (4.7 mmol) of dibromotriphenylphosphorane are added to a solution of 1.15 g (4.6 nmnol) of the alcohol obtained in Step C in 25 ml of anhydrous acetonitrile. The medium is stirred for 1 hour at ambient temperature; the solvent is then evaporated in vacuo. The residue obtained is taken up in a mixture of ether/hexane (1/1); the solid formed is then filtered off over Celite. Evaporation of the filtrate yields the brominated compound of the title in the form of a chestnut-brown syrup.

Step E: [6-(Pentyloxy)-2H-3-chromenyl]methanamine 1.25 g (6.75 mmol) of potassium phthalimide are added to a solution of 1.4 g (4.5 mmol) of the brominated compound obtained in Step D in 15 ml of DMF; the medium is then stirred overnight at ambient temperature and under argon. After evaporation of the solvent in vacuo, the residue obtained is taken up in water; the aqueous phase is then extracted with dichloromethane. The organic phase, dried over magnesium sulphate and then filtered, is concentrated in vacuo. Chromatography on a silica column (eluant:ethyl acetate/petroleum ether 10/90) allows access to the title phthalimide in the form of a white solid.

Melting point: 126° C.

Step F: [6-(Pentyloxy)-2H-3-chromenyl]methylamine

A solution of 1.2 g (3.3 mmol) of phthalimide and 0.7 ml (13.2 mmol) of hydrazine monohydrate in 10 ml of THF is heated at reflux for 4 hours and then allowed to cool. The solid formed is filtered off; the solvent is then evaporated in vacuo to yield the title amine in the form of a yellow solid.

Melting point: 52° C.

Step G: N-{[6-(Pentyloxy)-2H-3-chromenyl]methyl}acetamide 0.34 g (1.38 mmol) of the amine obtained in Step F is acetylated with acetic anhydride in pyridine according to the usual procedure. The crude product of that reaction is purified on a silica column (eluant:ethyl acetate) to yield the title acetamide in the form of a white solid.

Melting point: 97° C.
Elemental microanalysis:

|  | C | H | N |
|---|---|---|---|
| % Calculated | 70.56 | 8.01 | 4.84 |
| % Found | 70.84 | 7.89 | 4.80 |

EXAMPLE 56

N-{[6-(Pentyloxy)-2H-3-chromenyl]methyl}butanamide 0.37 g (1.5 mmol) of the amine obtained in Step F of Example 55 is condensed with butanoyl chloride according to the same procedure as in Example 54. Purification on a silica column (eluant:ethyl acetate/petroleum ether 50/50) allows isolation of the title amide in the form of a yellowish solid.

Melting point: 90° C.
Elemental microanalysis:

|  | C | H | N |
|---|---|---|---|
| % Calculated | 71.89 | 8.57 | 4.41 |
| % Found | 71.54 | 8.53 | 4.29 |

EXAMPLE 57

N-[2-(2,3-dihydrofuro[2',3':5,6]benzo[b][1,4]dioxin-8-yl)ethyl]acetamide

In a sealed tube, 5-iodo-2,3-dihydro-1,4-benzodioxin-6-ol (500 mg, 1.8 mmol) is dissolved in 5 ml of HMPA. Triethylamine (750 μl, 3 eq), CuI (343 mg, 1 eq), Pd(II) (38 mg, 0.03 eq) and N-[4-(1,1,1-trimethylsilyl)-3-butynyl]acetamide (667 mg; 2 eq) are added in succession. The reaction is heated at 90° C. for 12 hours. After cooling, filtration on a frit and rinsing with AcOEt are carried out. The batch is hydrolysed and extracted with AcOEt and the organic phase is dried over MgSO$_4$. After evaporation of the solvents, flash purification of the residue over silica is carried out (eluant:PE/AcOEt (8/2)). The title product is obtained in the form of a white solid.

Melting point: 117° C.
Elemental microanalysis:

|  | C | H | N |
|---|---|---|---|
| % Calculated | 64.35 | 5.79 | 5.36 |
| % Found | 64.30 | 5.96 | 5.46 |

EXAMPLE 58

N-[2-(2,3-Dihydrofuro[2',3':5,6]benzo[b][1,4]dioxin-9-yl)ethyl]acetamide

The procedure is analogous to that of Example 57 except for the amount of CuI (0.1 eq). That reaction leads to the formation of the silylated intermediate N-{2-[8-(1,1,1-trimethylsilyl)-2,3-dihydrofuro[2', 3':5,6]benzo[b][1,4]dioxin-9-yl]ethyl}acetamide (290 mg, 0.83 mmol), which is dissolved in CH$_2$Cl$_2$ (20 ml); AlCl$_3$ (443 mg, 4 eq) is then added thereto. After one hour of stirring, the batch is hydrolysed progressively and then extracted with CH$_2$Cl$_2$. After drying the organic phase over MgSO$_4$ and then evaporation, the residue is chromatographed on a silica column (eluant:AcOEt (100%)). After recrystallisation from an Et$_2$O/toluene mixture, the title compound is obtained.

Melting point: 112° C.
Elemental microanalysis:

|  | C | H | N |
|---|---|---|---|
| % Calculated | 64.35 | 5.79 | 5.36 |
| % Found | 64.50 | 5.93 | 5.27 |

EXAMPLE 59

N-[2-(8-Phenyl-2,3-dihydrofuro[2',3':5,6]benzo[b][1,4]dioxin-9-yl)ethyl]-acetamide The procedure is the same as for Example 58 with replacement of N-[4-(1,1,1-trimethylsilyl)-3-butynyl] acetamide with N-(4-phenyl-3-butynyl)acetamide.

Melting point: 192° C.
Elemental microanalysis:

|  | C | H | N |
|---|---|---|---|
| % Calculated | 71.20 | 5.67 | 4.15 |
| % Found | 71.44 | 5.74 | 4.23 |

EXAMPLE 60

N-[2-(6-Methoxy-2-phenyl-4H-4-chromenyl)ethyl]acetamide

Step A: 6-Methoxy-2-phenyl-4H-4-chromenecarbonitrile

The procedure is as in Preparation 15, starting from the compound obtained in Preparation 17.

Step B: 6-Methoxy-2-phenyl-4H-4-chromenecarbaldehyde

The title compound is obtained by reduction of the nitrile obtained in Step A with diisobutylaluminium hydride.

Step C: 2-(6-Methoxy-2-phenyl-4H-4-chromenyl)acetonitrile

The procedure is as in Preparation 15, starting from the compound obtained in Step B.

Step D: N-[2-(6-Methoxy-2-phenyl-4H-4-chromenyl)ethyl]acetamide

The procedure is as in Steps C and D of Example 1, starting from the compound obtained in Step C.

EXAMPLE 61

N-[2-(6-Methoxy-2-phenyl-2H-4-chromenyl)ethyl]acetamide

Step A: 6-Methoxy-2-phenyl-4-chromanone

The procedure is as in Step B of Example 1, starting from the compound obtained in Preparation 17.

Step B: 6-Methoxy-4-methylene-2-phenylchroman

The title compound is obtained according to a conventional Wittig reaction, starting from the compound obtained in Step A and methylene(triphenyl)phosphorane.

Step C: 4-(Bromomethyl)-6-methoxy-2-phenylchroman

The title compound is obtained by the action of NBS in a dioxane/$H_2O$ mixture on the compound obtained in Step B.

Step D: 2-(6-Methoxy-2-phenyl-3,4-dihydro-2H-4-chromenyl)acetonitrile

The procedure is as in Step C of Example 38, starting from the compound obtained in Step C.

Step E: N-[2-(6-Methoxy-2-phenyl-2H-4-chromenyl)ethyl]acetamide

The title product is obtained by proceeding as in Steps C and D of Example 1, starting from the compound obtained in Step D.

PHARMACOLOGICAL STUDY

EXAMPLE A

Acute Toxicity Study

The acute toxicity was evaluated after oral administration to groups each comprising 8 mice (26±2 grams). The animals were observed at regular intervals during the course of the first day, and daily for the two weeks following treatment. The $LD_{50}$ (dose that causes the death of 50% of the animals) was evaluated and demonstrated the low toxicity of the majority of the compounds of the invention.

EXAMPLE B

Melatonin Receptor Binding Study

1) Study on pars tuberalis cells of sheep

Melatonin receptor binding studies of the compounds of the invention were carried out according to conventional techniques on pars tuberalis cells of sheep. The pars tuberalis of the adenohypophysis is in fact characterised in mammals by a high density of melatonin receptors (Journal of Neuroendocrinology, 1, pp 1–4, 1989).

Protocol

1) Sheep pars tuberalis membranes are prepared and used as target tissue in saturation experiments to determine the binding capacities and affinities for 2-[$^{125}$I]-iodomelatonin.

2) Sheep pars tuberalis membranes are used as target tissue in competitive binding experiments using the various test compounds in comparison with melatonin.

Each experiment is carried out in triplicate and a range of different concentrations is tested for each compound. The results enable the determination, after statistical processing, of the binding affinities of the compound tested.

Results

The compounds of the invention appear to have a strong affinity for melatonin receptors.

2) Study on membranes of Chicken (*Gallus domesticus*) Brain Homogenate

The animals used are 12-day-old chickens (*Gallus domesticus*). They are sacrificed between 1 pm and 5 pm on the day of their arrival. The brains are removed quickly and frozen at −200° C. and then stored at −80° C. The membranes are prepared according to the method described by Yuan and Pang (Journal of Endocrinology, 128, pp 475–482, 1991). 2-[$^{125}$I]-iodomelatonin is incubated for 60 minutes at 25° C. in the presence of the membranes in a buffered solution of pH 7.4. At the end of that period, the membrane suspension is filtered (Whatman GF/C). The radioactivity retained on the filter is determined using a Beckman® LS 6000 liquid scintillation counter.

The products used are:

2-[$^{125}$I]-iodomelatonin melatonin current products novel molecules.

In primary screening, the molecules are tested at 2 concentrations ($10^{-7}$ and $10^{-5}$ M). Each result is the average of 3 independent measurements. The active molecules selected in accordance with the primary screening results are subjected to a quantitative determination of their efficacy ($IC_{50}$). They are used at 10 different concentrations.

The $IC_{50}$ values found for the preferred compounds of the invention show that the binding of the test compounds is very strong.

EXAMPLE C

Four Plate Test

The products of the invention are administered by the oesophageal route to groups each comprising ten mice. One group is given syrup of gum. Thirty minutes after administration of the products to be studied, the animals are placed in cages in which the floor is composed of four metal plates. Each time the animal passes from one plate to another it receives a slight electric shock (0.35 mA). The number of passages from one plate to another is recorded for one minute. After administration, the compounds of the invention significantly increase the number of passages from one plate to another, demonstrating the anxiolytic activity of the compounds of the invention.

EXAMPLE D

Action of the Compounds of the Invention on the Circadian Rhythms of Locomotive Activity of the Rat The involvement of melatonin in influencing, by day/night alternation, the majority of physiological, biochemical and behavioural circadian rhythms has made it possible to establish a pharmacological model for research into melatoninergic ligands. The effects of the molecules are tested on numerous parameters and, in particular, on the circadian rhythms of locomotive activity, which are a reliable indicator of the endogenous circadian clock activity. In this study, the effects of such molecules on a particular experimental model, namely the rat placed in temporal isolation (permanent darkness), are evaluated.

Experimental protocol

One-month-old Long Evans male rats are subjected, as soon as they arrive at the laboratory, to a light cycle of 12 hours' light per 24 hours (L/D 12:12).

After 2 to 3 weeks' adaptation, they are placed in cages fitted with a wheel connected to a recording system, in order to detect the phases of locomotive activity and thus monitor the circadian rhythms.

As soon as the rhythms recorded show a stable pattern during the light cycle L/D 12:12, the rats are placed in permanent darkness (D/D).

Two to three weeks later, when the free course (rhythm reflecting that of the endogenous clock) is clearly established, the rats are given a daily administration of the molecule to be tested.

The observations are made by means of visualisation of the rhythms of activity:
influence on the rhythms of activity by the light/dark cycle (L/D),
disappearance of the influence on the rhythms in permanent darkness,
influence on the activity by the daily administration of the molecule; transitory or durable effect.

A software package makes it possible:
to measure the duration and intensity of the activity, the period of the rhythm of the animals during free course and during treatment,
possibly to demonstrate by spectral analysis the existence of circadian and non-circadian (for example ultradian) components.

Results:

The compounds of the invention clearly appear to allow powerful action on the circadian rhythm via the melatoninergic system.

EXAMPLE E

Anti-arrhythmic Activity

Protocol (Ref: LAWSON J. W. et al. J. Pharmacol. Expert. Therap., 1968, 160, pp 22–31).

The test substance is administered intraperitoneally to a group of 3 mice 30 minutes before being subjected to anaesthesia with chloroform. The animals are then observed for 15 minutes. The absence of recording of arrhythmia and cardiac frequencies higher than 200 beats/min (control: 400–480 beats/min) in at least two animals indicates significant protection.

EXAMPLE F

Pharmaceutical Composition:Tablets

| | |
|---|---|
| 1000 tablets each comprising 5 mg of N-(9-methoxy-2,3-dihydro-1H-benzo[f]-chromen-2-yl)acetamide (Example 5) | 5 g |
| wheat starch | 20 g |
| maize starch | 20 g |
| lactose | 30 g |
| magnesium stearate | 2 g |
| silica | 1 g |
| hydroxypropyl cellulose | 2 g |

We claim:
1. A compound selected from those of formula (I):

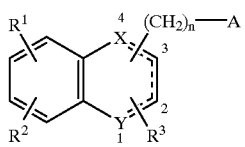

wherein
$R^1$ represents hydrogen, substituted or unsubstituted linear or branched ($C_1$–$C_6$)alkyl, substituted or unsubstituted linear or branched ($C_2$–$C_6$)alkenyl, substituted or unsubstituted linear or branched ($C_2$–$C_6$)alkynyl, substituted or unsubstituted ($C_3$–$C_8$)cycloalkyl, substituted or unsubstituted ($C_3$–$C_8$)cycloalkyl-($C_1$–$C_6$)alkyl in which the alkyl moiety is linear or branched, or $OR^4$ (wherein $R^4$ represents hydrogen, substituted or unsubstituted linear or branched ($C_1$–$C_6$)alkyl, substituted or unsubstituted linear or branched ($C_2$–$C_6$)alkenyl, substituted or unsubstituted linear or branched ($C_2$–$C_6$) alkynyl, aryl, aryl-($C_1$–$C_6$) alkyl in which the alkyl moiety is linear or branched, substituted or unsubstituted ($C_3$–$C_8$)cycloalkyl, or substituted or unsubstituted ($C_3$–$C_8$)cycloalkyl-($C_1$–$C_6$)alkyl in which the alkyl moiety is linear or branched),
$R^2$ represents hydrogen,
X represents oxygen, sulphur, $C(H)_q$ (wherein q is equal to 0, 1 or 2), SO, or $SO_2$,
when X is oxygen, sulphur, SO, or $SO_2$, Y must be $C(H)_q$ (wherein q is equal to 0, 1 or 2),
Y represents oxygen, sulphur, $C(H)_q$ (wherein q is equal to 0, 1 or 2), SO or $SO_2$,
when Y is oxygen, sulphur, SO, or $SO_2$, X must be $C(H)_q$ (wherein q is equal to 0, 1 or 2),
it being understood that X and Y cannot simultaneously represent $C(H)_q$ (wherein q is equal to 0, 1 or 2),
$R^3$ represents hydrogen, aryl, aryl-($C_1$–$C_6$)alkyl in which the alkyl moiety is linear or branched, or linear or branched ($C_1$–$C_6$) alkyl,
n is equal to 1, 2, 3, 4 or 5,
it being possible for the —$(CH_2)_n$— chain to be substituted by one or more halogen or one or more identical or different groups selected from linear or branched (C$_1$-C$_6$)alkyl, OH, linear or branched (C$_1$-C$_6$)alkylcarbonyl, and linear or branched (C$_1$-C$_6$)alkoxycarbonyl, A represents

NR$^5$R$^6$ wherein
R$^6$ represents hydrogen or linear or branched (C$_1$-C$_6$) alkyl,
R$^5$ represents

wherein Z represents oxygen or sulphur, and R$^7$ represents:
hydrogen, or
R$^8$ which represents substituted or unsubstituted linear or branched (C$_1$-C$_6$)alkyl, substituted or unsubstituted (C$_3$-C$_8$)cycloalkyl, substituted or unsubstituted (C$_3$-C$_8$)cycloalkyl-(C$_1$-C$_6$)alkyl in which the alkyl moiety is linear or branched, substituted or unsubstituted linear or branched (C$_2$-C$_6$)alkenyl, substituted or unsubstituted linear or branched (C$_2$-C$_6$)alkynyl, aryl, or aryl-(C$_1$-C$_6$)alkyl in which the alkyl moiety is linear or branched,
or NR$^8$R$^9$ wherein R$^9$ represents hydrogen or linear or branched (C$_1$-C$_6$)alkyl and R$^8$ is as defined hereinabove,
the symbol

⌐⌐ means that the bonds can be single or double, it being understood that two adjacent bonds cannot simultaneously be double and that the valency of the atoms is respected,
it being understood that:
the term "aryl" denotes phenyl or naphthyl optionally substituted by one or more halogen or one or more identical or different groups selected from OH, linear or branched (C$_1$-C$_6$)alkoxy, linear or branched (C$_1$-C$_6$)alkyl, cyano, nitro, amino, alkylamino, dialkylamino, and tahaloalkyl,
the term "substituted" used in respect of the terms "alkyl", "alkenyl" and "allynyl" means that the group is substituted by one or more halogen or one or more identical or different groups selected from OH, linear or branched (C$_1$-C$_6$)alkoxy, amino, alkylamino and dialkylamino,
the term "substituted" used in respect of the terms "cycloalkyl" and "cycloalkylalkyl" means that the cyclic moiety is substituted by one or more halogen or one or more identical or different groups selected from linear or branched (C$_1$-C$_6$)alkyl, linear or branched (C$_1$-C$_6$)alkoxy, hydroxy, oxo, amino, alkylamino, and dialkylamino,
provided that:
when the compound of formula (I) is a chroman compound (X represents CH$_2$, Y represents oxygen and R$^1$, R$^2$ and R$^3$ are as defined hereinabove and the bonds ══ are single), the group —(CH$_2$)$_n$—A is other than the following groups:

—CH$_2$—NHCOR$_e$ (wherein R$_e$ repesents cycloalkyl) in the 2-position of the chroman group,
when A represents NHCSNHR$^8$ and n is equal to 2, R$^8$ cannot represent aryl,
when X represents CH$_2$, A cannot represent urea or thiourea substituted by substituted or unsubstituted phenyl, its enantiomers and diastereoisomers, and addition salts thereof with a pharmaceutically-acceptable acid or base.

2. A compound selected from those of formula (I):

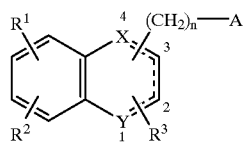

(I)

wherein:

R$^1$ represents hydrogen, substituted or unsubstituted linar or branched (C$_1$-C$_6$)alkyl, substituted or unsubstituted linear or branched (C$_2$-C$_6$)alkenyl, substituted or unsubstituted linear or branched (C$_{26}$)alkynyl, substituted or unsubstituted (C$_3$-C$_8$)cycloalkyl, substituted or unsubstituted (C$_3$-C$_8$)cycloalkyl-(C$_1$-C$_6$)alkyl in which the alkyl moiety is linear or branched, or OR$^4$ (wherein R$^4$ represents hydrogen, substituted or unsubstituted linear or branched (C$_1$-C$_6$)alkyl, substituted or unsubstituted linear or branched (C$_2$-C$_6$)alkenyl, substituted or unsubstituted linear or branched (C$_2$-C$_6$) alkynyl, aryl, aryl-(C$_1$-C$_6$)alkyl in which the alkyl moiety is linear or branched, substituted or unsubstituted (C$_3$-C$_8$)cycloalkyl, or substituted or unsubstituted (C$_3$-C$_8$)cycloalkyl-(C$_1$-C$_6$)alkyl in which the alkyl moiety is linear or branched), R$^2$ represents hydrogen, X represents oxygen, sulphur, C(H$_q$) (wherein q is equal to 0, 1 or 2), SO, or SO$_2$
when X is oxygen, sulphur, SO, or SO$_2$, Y must be C(H)$_q$ (wherein q is equal to 0, 1 or 2), Y represents oxygen, sulphur, C(H)$_q$ (wherein q is equal to 0, 1 or 2), SO or SO$_2$,
when Y is oxygen, sulphur, SO, or SO$_2$, X must be C(H)$_q$ (wherein q is equal to 0, 1 or 2), it being understood that X and Y cannot simultaneously represent C(H)$_q$ (wherein q is equal to 0, 1 or 2), R$^3$ represents hydrogen, aryl, aryl-(C$_1$-C$_6$)alkyl in which the alkyl moiety is linear or branched, or linear or branched (C$_1$-C$_6$)alkyl, n is equal to 1, 2, 3, 4 or 5, it being possible for the —(CH$_2$)$_n$— chain to be substituted by one or more halogen or one or more identical or different groups selected from linear or branched (C$_1$-C$_6$)alkyl, OH, linear or branched (C$_f$-C$_6$)alkoxy, linear or branched (C$_1$-C$_6$)alkylcarbonyl, and linear or branched (C$_1$-C$_6$) alkoxycarbonyl, A represents
NR$^5$R$^6$ wherein
R$^6$ represents hydrogen or linear or branched (C$_1$-C$_6$)alkyl, R⁵ represents

wherein Z represents oxygen or sulphur, and R⁷ represents:
hydrogen
R⁸ which represents substituted or unsubstituted linear or branched (C₁–C₆)alkyl, substituted or unsubstituted (C₃–C₈)cycloalkyl, substituted or unsubstituted (C₃–C₁)cycloalkyl-(C₁–C₆)alkyl in which the alkyl moiety is linear or branched, substituted or unsubstituted linear or branched (C₂–C₆)alkenyl, substituted or unsubstituted linear or branched (C₂–C₆)alkynyl, aryl, or aryl-(C₁–C₆)alkyl in which the alkyl moiety is linear or branched,
or NR⁸R⁹ wherein R⁹ represents hydrogen or linear or branched (C₁–C₆)alkyl and R⁸ is as defined hereinabove,
the symbol

means that the bonds can be single or double, it being understood that two adjacent bonds cannot simultaneously be double and that the valency of the atoms is respected,
it being understood that:
the term "aryl" denotes phenyl or naphthyl optionally substituted by one or more halogen or one or more identical or different groups selected from OH, linear or branched (C₁–C₆)alkoxy, linear or branched (C₁–C₆)alkyl, cyano, nitro, amino, alkylamino, dialkylaminno, and trihaloalkyl,
the term "substituted" used in respect of the terms "alkyl", "alkenyl" and "alkynyl" means that the group is substituted by one or more halogen or one or more identical or different groups selected from OH, linear or branched (C₁–C₆)alkoxy, amino, alkylamino and dialkylamino,
the term "substituted" used in resect of the terms "cycloalkyl" and "cycloalkylalkyl" means that the cyclic moiety is substituted by one or more halogen or one or more identical or different groups selected from linear or branched (C₁–C₆)alkyl, linear or branched (C₁–C₆)alkoxy, hydroxy, oxo, amino, alkylamnino, and dialkylamino,
provided that:
when the compound of formula (I) is a chroman compound (X represents CH₂, Y represents oxygen and R¹, R² and R³ are as defined hereinabove and the bonds ==== are single), the group —(CH₂)ₙ—A is other than the following groups: CH₂—NHCORₑ (wherein Rₑ represents cycloalkyl) in the 2-position of the chroman group,
when A represents NHCSNHR⁸ and n is equal to 2, R⁸ cannot represent aryl,
when X represents CH₂, A cannot represent urea or thiourea substituted by substituted or unsubstituted phenyl, its enantiomers and diastereoisomers, and addition salts thereof with a pharmaccmdcally-acceptable acid or base.

3. A compound of claim 1 wherein R¹ represents OR⁴, its enantiomers and diastereoisomers, and addition salts thereof with a pharmaceutically-acceptable acid or base.

4. A compound of claim 1 wherein X represents C(H)_q (wherein q is equal to 0, 1 or 2) and Y represents oxygen or sulphur, its enantiomers and diastereoisomers, and addition salts thereof with a pharmaceutically-acceptable acid or base.

5. A compound of claim 1 wherein R³ represents hydrogen, its enantiomers and diastereoisomers, and addition salts thereof with a pharmaceutically-acceptable acid or base.

6. A compound of claim 1 wherein R³ represents aryl, its enantiomers and diastereoisomers, and addition salts thereof with a pharmaceutically-acceptable acid or base.

7. A compound of claim 1 which is N-[2-(6-methoxy-3,4-dihydro-2H-chromenyl)ethyl]acetamide, its enantiomers and diastereoisomers, and addition salts thereof with a pharmaceutically-acceptable acid or base.

8. A compound of claim 1 which is N-[(6-methoxy-2H-3-chromenyl)methyl]butanamide, its enantiomers and diastereoisomers, and addition salts thereof with a pharmaceutically-acceptable acid or base.

9. A pharmaceutical composition comprising as active ingredient at least one compound of claim 1 or an addition salt thereof with a pharmaceutically-acceptable acid or base in combination with one or more pharmaceutically-acceptable excipients.

10. A method of treating a disorder of the melatoninergic system of a living animal body comprising the step of administering to the living animal body an amount of a compound of claim 1 which is effective for alleviation of said disorder.

11. A compound of claim 1 which is a dihydrochromene or a chromene, their enantiomers and diastereoisomers, and addition salts thereof with a pharmaceutically acceptable acid or base.

* * * * *

UNITED STATES PATENT AND TRADEMARK OFFICE
CERTIFICATE OF CORRECTION

PATENT NO.    : 6,313,160 B1
DATED         : November 6, 2001
INVENTOR(S)   : Gerald Guillaumet et al.

Page 1 of 1

It is certified that error appears in the above-identified patent and that said Letters Patent is hereby corrected as shown below:

<u>Column 59,</u>
Line 48, "tahaloalkyl" should be -- trihaloalkyl --.

Signed and Sealed this

Nineteenth Day of March, 2002

Attest:

JAMES E. ROGAN
Attesting Officer
Director of the United States Patent and Trademark Office